United States Patent
Lyu et al.

(10) Patent No.: US 7,575,817 B2
(45) Date of Patent: Aug. 18, 2009

(54) CYCLOMETALATED TRANSITION METAL COMPLEX AND ORGANIC ELECTROLUMINESCENT DEVICE USING THE SAME

(75) Inventors: Yi-Yeol Lyu, Yongin-si (KR); Young-Hun Byun, Yongin-si (KR); Das Rupasree Ragini, Suwon-si (KR); Eun-Sil Han, Yongin-si (KR); Seok Chang, Daejeon-si (KR); Lyong-Sun Pu, Suwon-si (KR); Jong-Hyoup Lee, Seoul (KR)

(73) Assignee: Samsung Mobile Display Co., Ltd., Yongin, Gyunggi-Do (KR)

(*) Notice: Subject to any disclaimer, the term of this patent is extended or adjusted under 35 U.S.C. 154(b) by 668 days.

(21) Appl. No.: 11/156,604

(22) Filed: Jun. 21, 2005

(65) Prior Publication Data
US 2006/0073358 A1 Apr. 6, 2006

(30) Foreign Application Priority Data
Oct. 1, 2004 (KR) .................. 10-2004-0078263

(51) Int. Cl.
*H01L 51/54* (2006.01)
*C09K 11/06* (2006.01)
*C07D 213/02* (2006.01)
*C07F 9/02* (2006.01)

(52) U.S. Cl. .................. 428/690; 428/917; 313/504; 313/506; 548/101; 548/103; 546/4; 257/102

(58) Field of Classification Search ............ 428/690, 428/917; 313/504, 506; 257/40, 102, 103, 257/E51.044; 252/301.16; 546/2, 4, 10; 556/13, 18, 19, 20; 548/101, 103
See application file for complete search history.

(56) References Cited

U.S. PATENT DOCUMENTS

| 2002/0048689 A1 | 4/2002 | Igarashi et al. |
| 2002/0064681 A1 | 5/2002 | Takiguchi et al. |
| 2002/0182441 A1 | 12/2002 | Lamansky et al. |
| 2003/0173896 A1* | 9/2003 | Grushin et al. ............... 313/506 |
| 2004/0001969 A1* | 1/2004 | Cosimbescu et al. ......... 428/690 |

FOREIGN PATENT DOCUMENTS

| JP | 2005/097263 A * | 4/2005 |
| WO | WO 02/15645 | 2/2002 |

OTHER PUBLICATIONS

Machine Translation of JP 2005/097263 A (2005).*
Druliner et al. "A new class of nickel hydrides. HNiL3CN." J. Am. Chem. Soc. 1976, pp. 2156-2160.*

* cited by examiner

*Primary Examiner*—D. Lawrence Tarazano
*Assistant Examiner*—Michael Wilson
(74) *Attorney, Agent, or Firm*—Robert E. Bushnell, Esq.

(57) ABSTRACT

A cyclometalated transition metal complex emitting phosphorescence of high efficiency and an organic electroluminescent display device employing the same are provided. The cyclometalated transition metal complex has a transition metal atom and a phosphorus ligand having at least one alkylene oxide and a phosphorus atom. The phosphorus atom is bound to the transition metal atom. The cyclometalated transition metal complex can be employed when forming an organic film of an organic electroluminescent display device, can emit light at a wavelength range of 400 nm to 650 nm, and can emit white light as well when used with a green light emitting material and a red light emitting material.

19 Claims, 4 Drawing Sheets

CYCLOMETALATED TRANSITION METAL COMPLEX AND ORGANIC ELECTROLUMINESCENT DEVICE USING THE SAME

CLAIM OF PRIORITY

This application claims the priority of Korean Patent Application No. 10-2004-0078263, filed on Oct. 1, 2004, in the Korean Intellectual Property Office, the disclosure of which is incorporated herein in its entirety by reference.

BACKGROUND OF THE INVENTION

1. Field of the Invention

The present invention relates to a cyclometalated transition metal complex and an organic electroluminescent display device using the same, and more particularly, to a cyclometalated transition metal complex that can emit light at a wavelength range of from blue to red region from triplet metal-to-ligand charge-transfer (MLCT), and an organic electroluminescent display device that applies the complex as an organic film forming material.

2. Description of the Related Art

An organic electroluminescent display device (organic EL display device) is an active light-emitting display device employing the phenomenon that when an electric current is applied to a thin film (hereinafter referred to as "organic film") composed of a fluorescent or phosphorescent organic compound, the fluorescent or the phosphorescent organic compound emits light in response to the recombination of electrons and holes in the organic film. The display device is light, has a structure of which the component is simple and its manufacturing process is simple, ensures wide view angle with high image quality. Further, the display has the electrical properties suitable for portable electronic devices since it can embody high color purity and moving picture, and can be driven by low consuming power and low voltage.

A general organic electroluminescent display device has a structure that an anode is formed at the upper part of a substrate, and a hole transporting layer, a light emitting layer, an electron transporting layer and a cathode are sequentially formed at the upper part of the anode. Herein, the hole-transporting layer, the light emitting layer and the electron-transporting layer are organic films composed of organic compounds. The driving principle for the organic electroluminescent display device having such a structure is as follows. When voltage is applied between the anode and the cathode, a hole injected from an anode is migrated to a light-emitting layer via a hole-transporting layer. Meanwhile, an electron is injected from a cathode into a light-emitting layer via an electron-transporting layer, and carriers are recombined at the area of the light-emitting layer to form an exiton. The exiton emits light with a wavelength corresponding to a band gap of a material when the exiton decays radiatively.

The light emitting layer-forming materials are classified into a fluorescent material using singlet exitons and a phosphorescent material using triplet exitons, according to their light-emitting mechanism. The light emitting layer is formed of a fluorescent or phosphorescent material alone or an appropriate host material doped with the fluorescent or phosphorescent material, and as electrons are excited, singlet exitons and triplet excitons are formed in the host. Herein, the statistic forming ratio of the singlet exitons to the triplet excitons is 1:3.

The organic electroluminescent display device using a fluorescent material as a light emitting layer-forming material has a disadvantage that the triplet excitons formed in the host are consumed, while the device using a phosphorescent material as a light emitting layer-forming material has an advantage that both of the singlet excitons and the triplet excitons can be used, and thus the internal quantum efficiency can reach 100%. Accordingly, when a phosphorescent material is used as a light emitting layer-forming material, the phosphorescent material can possess even higher light emitting efficiency than when a fluorescent material is used.

When a heavy metal such as Ir, Pt, Rh, Pd, etc. is incorporated into an organic molecule, triplet state and singlet state are mixed through spin-orbital coupling occurred by the heavy metal atom effect. Due to this, the transition that had been blocked is possible, and the phosphorescence can be occurred efficiently even at room temperature.

Recently, a green material or a red material of high efficiency employing the phosphorescence of which the internal quantum efficiency reaches 100% was developed.

Although several materials employing transition metal compounds comprising transition metals such as an iridium, a platinum, etc. as a highly efficient luminescent material employing phosphorescence are reported, the materials that satisfy the properties required for applying to full color display of high efficiency or white light emitting of low consuming power are limited to green and red region, and a phosphorescent material suitable for blue region is not developed. For such reason, there is an obstacle in developing a phosphorescent full color device.

To solve such problems, a blue light emitting material is developing (WO02/15645 A1, US 2002/0064681 A1). Further, an organic metal complex, incorporating a bulky functional group that can make HOMO-LUMO difference large by changing the molecular geometry, or a functional group that has strong ligand field (e.g., cyano group), was developed. Besides, an iridium complex represented by formula $Ir(ppy)_2P(ph)_3Y$ (wherein Y=Cl or CN) (US 2002/0182441 A1), and an iridium (III) complex having a cyclometalated ligand, a chelating diphosphine, a chlorine and a cyano group (US 2002/0048689 A1) were developed. Further, the US Serial No. 2002-0048689 discloses a luminescent device comprising a compound having a transition metal atom-phosphorus atom bond as an organic compound constituting a light-emitting layer.

SUMMARY OF THE INVENTION

It is therefore an object of the present invention to provide a blue light emitting material.

It is another object of the present invention to provide an improved light-emitting device.

It is a further object of the present invention to provide a cyclometalated transition metal complex that can emit light at a wavelength range of from blue to red region more efficiently from triplet metal-to-ligand charge-transfer (MLCT).

It is also another object of the present invention to provide an organic electroluminescent display device that can emit light at a wavelength range of from blue to red region more efficiently.

The present invention provides, in one aspect, a cyclometalated transition metal complex represented by formula I below:

$$[C^\wedge N]_{n1}M[P(Y^1)_{n2}(R^1)_{3-n2}]_{3-n1}X \qquad (I)$$

wherein M is a transition metal;
C^N is a cyclometalated ligand;
n1 is 1 or 2;
n2 is an integer of 1 to 3;

$Y^1$ is an alkylene oxide represented by formula II below;

$$—(OR^2)_{n3}OR^3 \quad (II)$$

wherein $R^2$ is a $C_2$-$C_{10}$ alkylene;

$R^3$ is a hydrogen atom, a $C_1$-$C_{30}$ alkyl group, a $C_5$-$C_{14}$ cycloalkyl group, a $C_5$-$C_{20}$ aryl group, a $C_3$-$C_{15}$ heterocyclic or methacrylate group;

n3 is an integer of 1 to 21;

$R^1$ is a hydrogen atom, an alkyl group, an alkynyl group, an aryl group, an amino group, an alkoxy group, an aryloxy group, an anacyl group, an alkoxycarbonyl group, an acyloxy group, an acylamino group, an alkoxycarbonylamino group, an aryloxycarbonylamino group, a sulfonylamino group, a sulfamoyl group, a carbamoyl group, an arylthio group, a heteroarylthio group, a sulfonyl group, a sulfinyl group, an ureido group, a phosphoramido group, a hydroxy group, a mercapto group, a halogen group, a cyano group, a sulfo group, a carboxy group, a nitro group, a hydroxaminic group, a heterocyclic group, a silyl group, or a phosphino group; and X is selected from the group consisting of Cl, OCN, CN, SCN, P(Ph)$_2$, R'COOH, R'CONH, R'NH, a pyrazole, a substituted or unsubstituted alkyl, alkoxy or aryloxy group, NR'H, NR'$_2$, OH, SH and a sulfonic acid group, wherein R' is a $C_1$-$C_{10}$ alkyl group, a $C_5$-$C_{14}$ cycloalkyl group or a $C_5$-$C_{14}$ aryl group.

It is preferred that M is Ru, Rh, Ir, Os, Pt or Au.

The present invention also provides a light-emitting device including a pair of electrodes and an organic layer interposed between the electrodes, the organic layer including a cyclometalated transition metal complex having a transition metal atom and a phosphorus ligand having at least one alkylene oxide and a phosphorus atom bound to the transition metal atom.

The present invention provides, in another aspect, a light-emitting device, particularly an organic electroluminescent display device, including an organic film between a pair of electrodes, wherein the organic film comprises a cyclometalated transition metal complex represented by the formula I.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, in which.

DETAILED DESCRIPTION OF THE INVENTION

Figure 1:
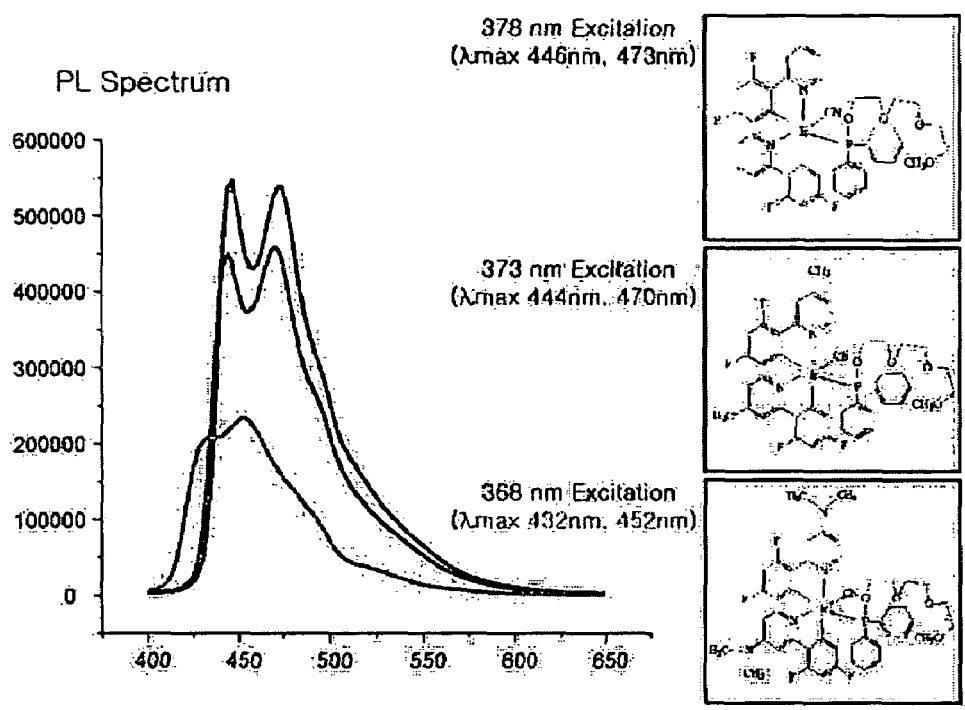
FIG. 1 is a photoluminescence (PL) spectrum of the compounds according to the examples 1, 3 and 5 of the present invention.

Hereinafter, the present invention will be described in more detail with reference to the embodiments thereof.

A cyclometalated transition metal complex according to the present invention provides an organic electroluminescent display device that has excellent stability and can emit blue light through binding a phosphorus atom, which is of a phosphorus ligand having at least one alkyleneoxide group, with a transition metal.

The cyclometalated transition metal complex according to the present invention has a structure represented by the formula I below:

$$[C^{\wedge}N]_{n1}M[P(Y^1)_{n2}(R^1)_{3-n2}]_{3-n1}X \quad (I)$$

wherein M is a transition metal of Ru, Rh, Ir, Os, Pt or Au;

$C^{\wedge}N$ is a cyclometalated ligand;

n1 is 1 or 2;

n2 is an integer of 1 to 3;

$Y^1$ is an alkylene oxide represented by formula II below;

$$—(OR^2)_{n3}OR^3 \quad (II)$$

wherein $R^2$ is a $C_2$-$C_{10}$ alkylene;

$R^3$ is a hydrogen atom, a $C_1$-$C_{30}$ alkyl group, a $C_5$-$C_{14}$ cycloalkyl group, a $C_5$-$C_{20}$ aryl group, a $C_3$-$C_{15}$ heterocyclic or methacrylate group;

n3 is an integer of 1 to 21;

$R^1$ is a hydrogen atom, an alkyl group, an alkynyl group, an aryl group, an amino group, an alkoxy group, an aryloxy group, an anacyl group, an alkoxycarbonyl group, an acyloxy group, an acylamino group, an alkoxycarbonylamino group, an aryloxycarbonylamino group, a sulfonylamino group, a sulfamoyl group, a carbamoyl group, an arylthio group, a heteroarylthio group, a sulfonyl group, a sulfinyl group, an ureido group, a phosphoramido group, a hydroxy group, a mercapto group, a halogen atom, a cyano group, a sulfo group, a carboxy group, a nitro group, a hydroxaminic group, a heterocyclic group, a silyl group, or a phosphino group; and X is selected from the group consisting of Cl, OCN, CN, SCN, P(Ph)$_2$, R'COOH, R'CONH, R'NH, a pyrazole, a substituted or unsubstituted alkyl, alkoxy or aryloxy group, NR'H, NR'$_2$, OH, SH and a sulfonic acid group, wherein R' is a $C_1$-$C_{10}$ alkyl group, a $C_5$-$C_{14}$ cycloalkyl group or a $C_5$-$C_{14}$ aryl group.

A cyclometalated transition metal complex represented by the formula I according to the present invention has a bond of a phosphorus atom, which is of a phosphorus ligand having at least one alkylene oxide group, and a transition metal atom, thereby emitting blue light efficiently and stably. Further, the bond of a phosphorus atom and a transition metal atom is stronger than the bond of a nitrogen atom of prior transition metal complex and a transition metal atom, and accordingly its heat stability is excellent.

By binding a phosphorus atom, which is of a phosphorus ligand having at least one alkylene oxide group, to a transition metal atom, the cyclometalated transition metal complex according to the present invention has excellent heat stability, has light-emitting wavelength migrated to blue region, and has excellent light-emitting efficiency, compared to prior iridium complex having a bond of a transition metal and a phosphorus atom.

The alkylene oxide group can be represented by the formula II, wherein n3 is an integer of 1 to 21, preferably an integer of 1 to 15, and more preferably an integer of 1 to 8. However, when n3 is larger than 21, that is not preferable in terms of the synthesis of a metal compound and light-emitting efficiency since a high molecular weight alkylene oxide is bound.

In the formula II, $R^2$ is a $C_2$-$C_{10}$ alkylene group, preferably a $C_2$-$C_5$ alkylene group, and more preferably a $C_2$-$C_3$ alkylene group. Herein, even when n3 is a long chain alkylene oxide group, steric hindrance is not suffered, and thus the substitution is easy.

In the formula II, $R^3$ is a hydrogen atom, a $C_1$-$C_{30}$ alkyl group, a $C_5$-$C_{14}$ cycloalkyl group, a $C_5$-$C_{20}$ aryl group, a $C_3$-$C_{15}$ heterocyclic or methacrylate group. It is preferred that $R^3$ is a $C_1$-$C_5$ alkyl group, a $C_5$-$C_{10}$ cycloalkyl group, a $C_6$-$C_{15}$ aryl group, and a $C_3$-$C_{10}$ heterocyclic or methacrylate group.

In the formula I, 1 to 3 alkylene oxide groups can be substituted on a phosphorus atom (i.e., n2 is an integer of 1 to 3). The more the alkylene oxide is substituted, the better the solubility is, and the more advantageous in emitting blue light.

It is preferred that, in the formula I, $R^1$ is a hydrogen atom, a $C_6$-$C_{30}$ aryl group, a $C_6$-$C_{30}$ aryloxy group, a $C_7$-$C_{30}$ aryloxycarbonyl group, a $C_4$-$C_{30}$ heteroaryl group, a $C_4$-$C_{30}$ thioaryl group, a $C_6$-$C_{30}$ aralkyl group, a $C_6$-$C_{30}$ heteroaralkyl group, or a $C_7$-$C_{30}$ aralkenyl group. It is more preferred that $R^1$ is a $C_6$-$C_{20}$ aryl group, a $C_6$-$C_{20}$ aryloxy group, a $C_7$-$C_{20}$ aryloxycarbonyl group, a $C_4$-$C_{20}$ heteroaryl group, a $C_4$-$C_{20}$ thioaryl group, a $C_6$-$C_{20}$ aralkyl group, a $C_6$-$C_{20}$ heteroaralkyl group, a $C_7$-$C_{20}$ aralkenyl group. It is much more preferred that $R^1$ is a $C_6$-$C_{12}$ aryl group, a $C_6$-$C_{12}$ aryloxy group, a $C_7$-$C_{12}$ aryloxycarbonyl group, a $C_4$-$C_{11}$ heteroaryl group, a $C_5$-$C_{11}$ thioaryl group, a $C_7$-$C_{13}$ aralkyl group, a $C_6$-$C_{12}$ heteroaralkyl group, a $C_7$-$C_{14}$ aralkenyl group.

In the formula I, is any one group selected from the group consisting of Cl, OCN, CN, SCN, P(Ph)$_2$, R'COOH, R'CONH, R'NH, a pyrazole, a substituted or unsubstituted alkyl, alkoxy or aryloxy group, NR'H, NR'$_2$, OH, SH and a sulfonic acid group, wherein R' is a $C_1$-$C_{10}$ alkyl group, a $C_5$-$C_{14}$ cycloalkyl group or a $C_5$-$C_{14}$ aryl group.

Preferably, X is Cl, CN, SCN or OCN.

In the formula I, the number of the cyclometalated ligand represented by (CAN) may be one or two, and when the number of the ligand is two, the ligands may be each other the same or different. It is preferred that the ligand may be any one selected from the group consisting of the formulae IIIa through IIIz below:

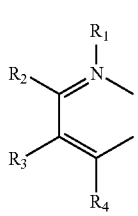

IIIa

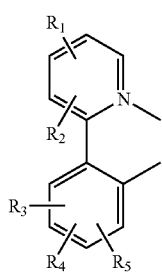

IIIb

-continued

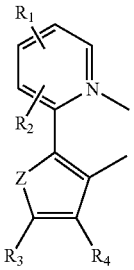

IIIc

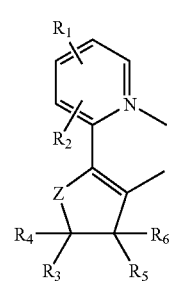

IIId

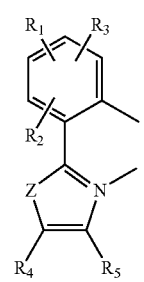

IIIe

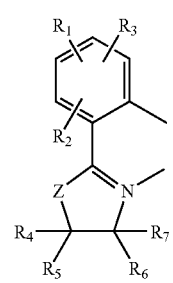

IIIf

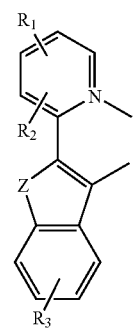

IIIg

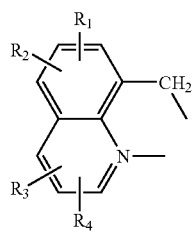
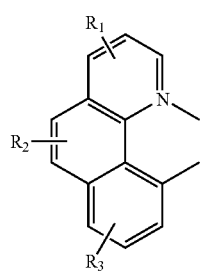
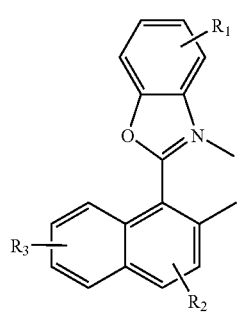
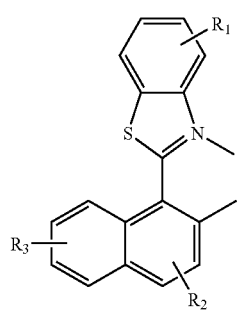
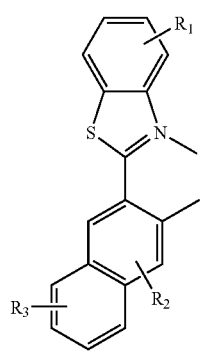
IIIh
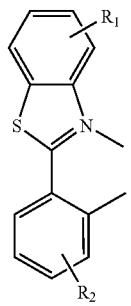
IIIi
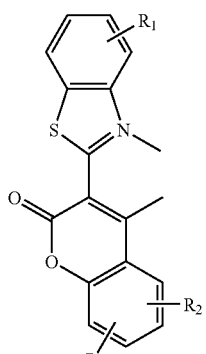
IIIj
IIIk
IIIl
IIIm
IIIn
IIIo
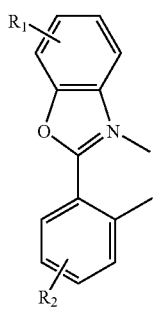
IIIp
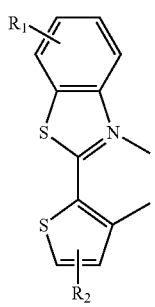
IIIq
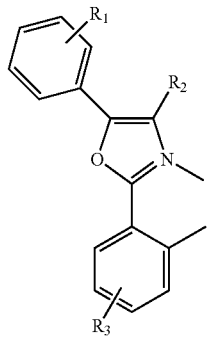

-continued

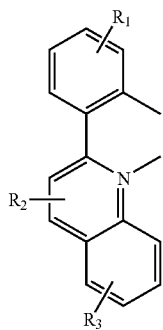

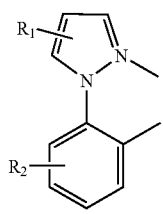

IIIs

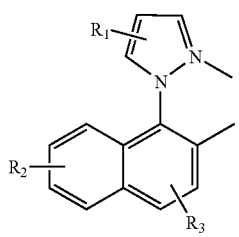

IIIt

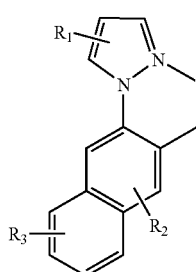

IIIu

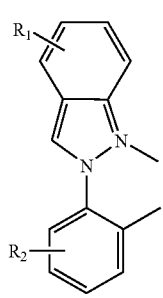

IIIv

-continued

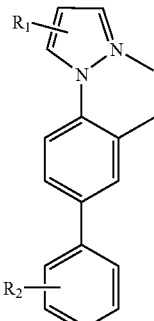

IIIr

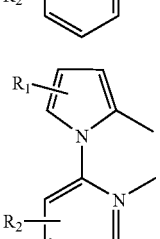

IIIw

IIIx

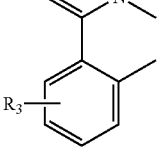

IIIy

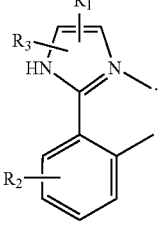

IIIz

In the formulae above, Z is S, O or NR$_1$,

R$_1$, R$_2$, R$_3$, R$_4$, R$_5$ and R$_6$ may be each independently any one selected from the group consisting of a hydrogen atom, a halogen atom, CN, a silyl group, an alkyl group, an aryl group, an arylene group, an amino group, an alkoxy group, an aryloxy group, a heterocyclicoxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclicthio group, a sulfonyl group, a sulfinyl group, an ureido group, a phosphor amide group, a sulfino group, a hydrazino group, an imino group, a heterocyclic group, a silyloxy group, a hydroxamine group, a nitro group, a hydroxyl group, a mercapto group, a sulfo group, a carboxyl group and a nitro group, and at least two of R$_1$, R$_2$, R$_3$, R$_4$, R$_5$ and R$_6$ may be bound each other.

The cyclometalated transition metal complexes represented by the formula I may be specifically the compounds represented by the formulae IVa through IVi, however, are not limited to these:
IVa
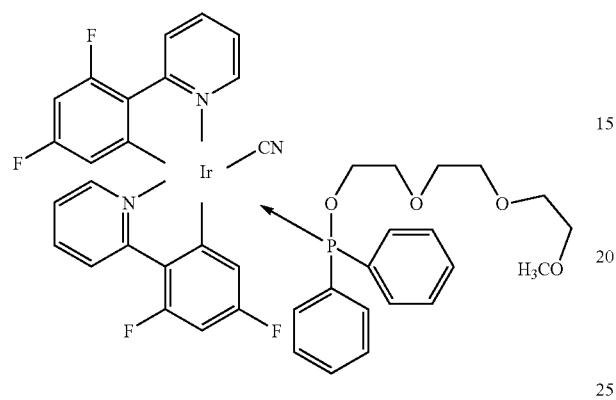
IVb
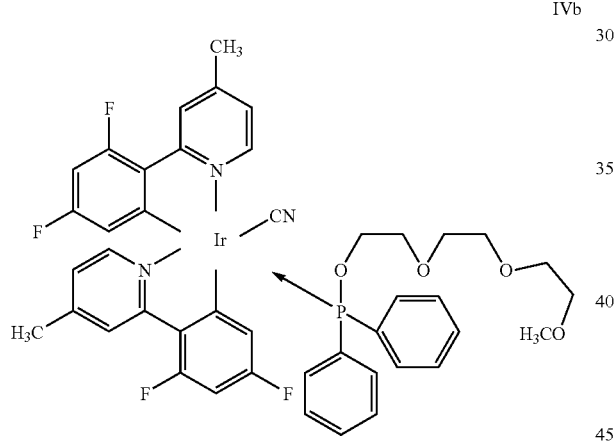
IVc
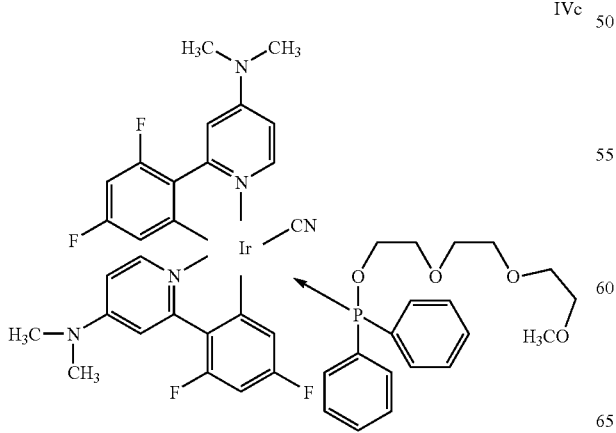
IVd
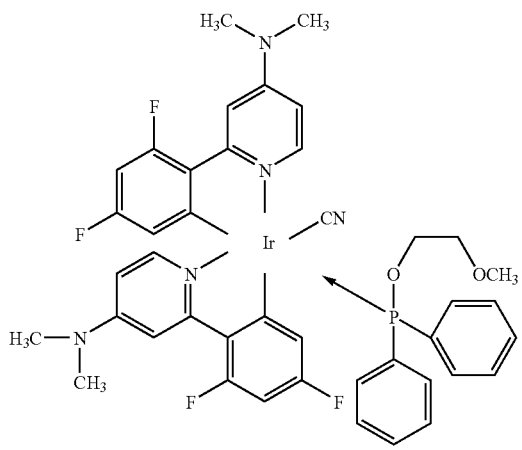
IVe
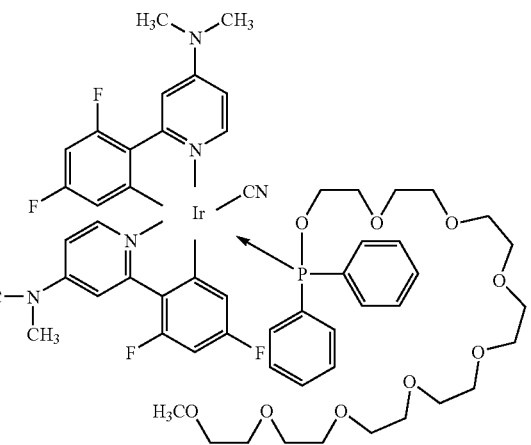
IVf
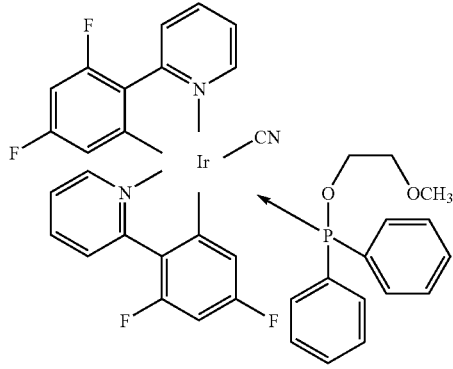

-continued

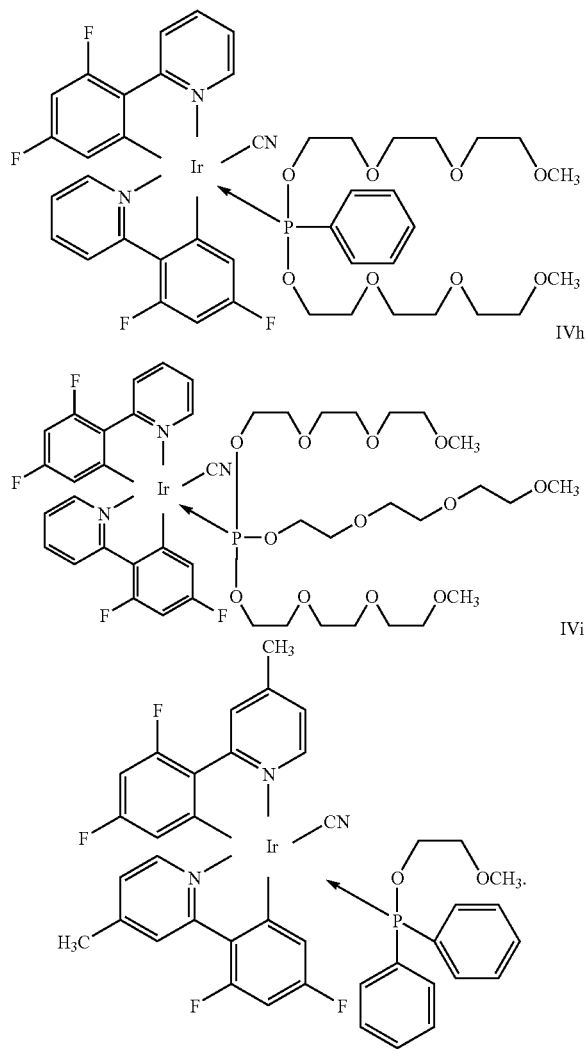

The transition metal complex according to the present invention has light-emitting property at a wavelength range of 400 nm to 650 nm.

The transition metal complex according to the present invention can be synthesized by using the starting material [Ir(C^N)$_2$Cl]$_2$ derivative that provides a cyclometalated moiety according to the method reported by Watts and his colleagues (F. O. Garces, R. J. Watts, Inorg. Chem. 1988, (35), 2450), which is incorporate herein by reference.

Hereinafter, the synthetic method will be described concerning the synthetic pathways of an iridium complex according to an embodiment of the present invention.

The starting material [Ir(C^N)$_2$Cl]$_2$ derivative and a phosphorus compound having at least one alkyleneoxide synthesized as in reaction scheme I below were mixed with a solvent such as a 1,2-dichloromethane, a methylene chloride, THF, etc., and the mixture was stirred for 2 to 48 hours at room temperature to obtain a (C^N)$_2$Ir[P[(OR$^2$)$_{n3}$OR$^3$]$_3$X, (C^N)$_2$Ir[P[(OR$^2$)$_{n3}$OR$^3$]R$^1$$_2$X, or (C^N)$_2$Ir[P[(OR$^2$)$_{n3}$OR$^3$]$_2$R$^1$X compound:

H—(OR$^2$)$_{n3}$OR$^3$+ClP(R$^1$)$_2$→P[(OR$^2$)$_{n3}$OR$^3$](R$^1$)$_2$

H—(OR$^2$)$_{n3}$OR$^3$+Cl$_2$P(R$^1$)→P[(OR$^2$)$_{n3}$OR$^3$]$_2$(R$^1$)

H—(OR$^2$)$_{n3}$OR$^3$+Cl$_3$P→P[(OR$^2$)$_{n3}$OR$^3$]$_3$     Reaction scheme I In the reaction scheme I, R$^1$, R$^2$, R$^3$, and n3 are the same as defined in the formula I and formula 2.

The organic electroluminescent device according to the present invention is prepared by forming an organic film, particularly a light emitting layer employing the cyclometalated transition metal complex according to the present invention. The transition metal complex represented by the Formula I is very useful as a phosphorescent dopant material that is a light emitting layer-forming material, and provides excellent light-emitting properties in the range of blue wavelengths.

When the cyclometalated transition metal complex according to the present invention is used as a phosphorescent dopant, an organic film may further comprise at least one selected from the group consisting of at least one of polymer hosts, a mixed host of a polymer and a low molecular weight compound, a low molecular weight host, and a non-luminescent polymer matrix. Herein, any materials that are typically used for forming a light-emitting layer for an organic electroluminescent device can be used as the polymer host, the low molecular weight host and a non-luminescent polymer matrix. The polymer host includes a polyvinylcarbazole (PVK) and polyfluorene, and the low molecular weight host that includes a 4,4'-N,N'-dicarbazole-biphenyl (CBP), a 4,4'-bis[9-(3,6-biphenylcarbazolyl)]-1,1'-biphenyl, a 9,10-bis[(2',7'-t-butyl)-9',9''-spiro bifluorenyl anthracene, and a tetrafluorene and the like. The non-luminescent polymer matrix includes a polymethylmethacrylate and a polystyrene, etc., however, is not limited to these.

The amount of the cyclometalated transition metal complex according to the present invention may be 1 to 30 parts by weight, based on 100 parts by weight of the total weights of the light-emitting layer-forming material. The incorporation of such a transition metal complex into the light-emitting layer can be carried out by vacuum vapor deposition, sputtering, printing, coating, ink jetting, or a method using electronic beam, etc.

Further, the transition metal complex according to the present invention can emit white light by using a green light-emitting material and a red light-emitting material together.

The thickness of the organic film may be 30 to 100 nm. The organic film used herein refers to a film of an organic compound, which is formed between a pair of electrodes in an organic electroluminescent display device, such as an electron transporting layer and a hole transporting layer, in addition to a light emitting layer. Such an organic electroluminescent display device can have commonly known various structures, such as anode/light emitting layer/cathode, anode/buffer layer/light emitting layer/cathode, anode/hole transporting layer/light emitting layer/cathode, anode/buffer layer/hole transporting layer/light emitting layer/cathode, anode/buffer layer/hole transporting layer/light emitting layer/electron transporting layer/cathode, anode/buffer layer/hole transporting layer/light emitting layer/hole blocking layer/cathode and the like, but the structures are not limited to these.

The buffer layer can be composed of a material commonly used in the art, and may be composed of a copper phthalocyanine, a polythiophene, a polyaniline, a polyacetylene, a polypyrrole, a polyphenylene vinylene or their derivatives, however, the material is not limited to these examples.

The hole transporting layer can be composed of a material commonly used in the art, and may be composed of, but is not limited to, a polytriphenylamine.

The electron transporting layer can be composed of a material commonly used in the art, and may be composed of, but is not limited to, a polyoxadiazole.

The hole blocking layer can be composed of a material commonly used in the art, and may be composed of, but is not limited to, LiF, $BaF_2$ or $MgF_2$ and the like.

The organic electroluminescent display device according to the present invention can be prepared by a common method of manufacturing an organic electroluminescent display device employing common luminescent materials, and thus does not need any special apparatuses or processes.

The cyclometalated transition metal complex can emit light at a wavelength range of 400 nm to 650 nm. The light emitting diode employing such a cyclometalated transition metal complex can be used in light source illumination, backlight, an outdoor bulletin board, optical communication, and interior decoration, etc.

Thus, the present invention will be described in greater detail with reference to the following examples. The following examples are for illustrative purposes and are not intended to limit the scope of the invention.

EXAMPLES

Reference Example 1

Synthesis of $F_2$ppy Dimer

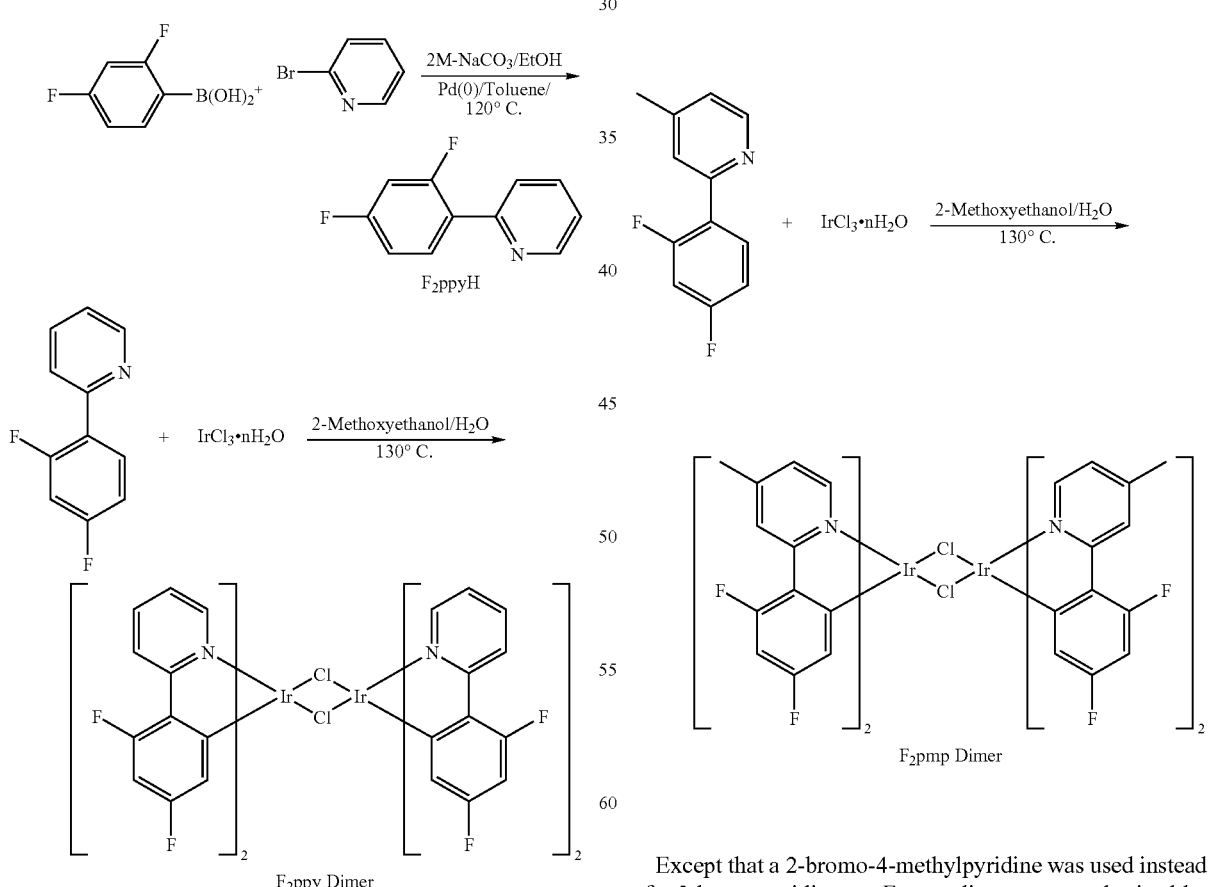

F$_2$ppy Dimer

To a 500 ml flask with a side arm, 19.85 g (1.25×10$^4$ mmol) of 2-bromopyridine, 25.00 g (1.58×10$^4$ mmol) of a 2,4-difluorophenyl boronic acid, 100 ml of a toluene, 48 ml of an ethanol and 2M sodium carbonate solution in 95 ml of water were added, and the mixture was agitated under nitrogen atmosphere at room temperature. Then, 4.53 g (3.92 mmol) of a tetrakis(triphenylphosphine) palladium(0) were added to the reaction mixture, and the mixture was refluxed under the nitrogen atmosphere for 15 hrs in the dark.

After the temperature of the reaction mixture was returned to room temperature on completion of the reaction, an organic layer was extracted using ethyl acetate and water. Then, the extract was separated by column chromatography (toluene: hexane=10:1) to obtain a pale brown liquid (F$_2$ppyH).

$^1$H-NMR(CD$_2$Cl$_2$, ppm): 8.69 (d, 1H), 8.03 (m, 1H), 7.70 (m, 2H), 7.27 (m, 1H), 7.00 (m, 2H).

By using 2-(4,6-difluorophenylpyridine) monomer synthesized according to the procedure and IrCl$_3$·nH$_2$O, a yellow powder F$_2$ppy dimer was synthesized. Herein, the synthesis was performed with reference to J. Am. Che. Soc., 1984, 106, 6647-6653.

$^1$H-NMR(CD$_2$Cl$_2$, ppm): 9.1 (d, 4H), 8.3 (d, 4H), 7.9 (t, 4H), 6.9 (m, 4H), 6.5 (m, 4H), 5.3 (d, 4H).

Reference Example 2

Synthesis of F$_2$pmp Dimer

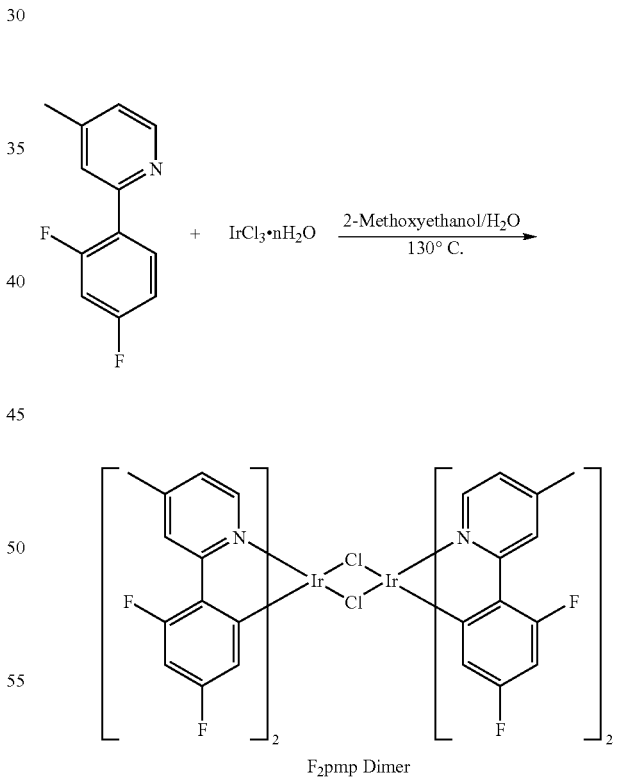

F$_2$pmp Dimer

Except that a 2-bromo-4-methylpyridine was used instead of a 2-bromopyridine, an F$_2$pmp dimer was synthesized by using the same method as in the reference example 1.

$^1$H-NMR(CD$_2$Cl$_2$, ppm): 8.9 (d, 4H), 8.1 (s, 4H), 6.6 (d, 4H), 6.3 (m, 4H), 5.3 (d, 4H), 2.6 (s, 12H).

Reference Example 3

Synthesis of DMAF$_2$ppy Dimer

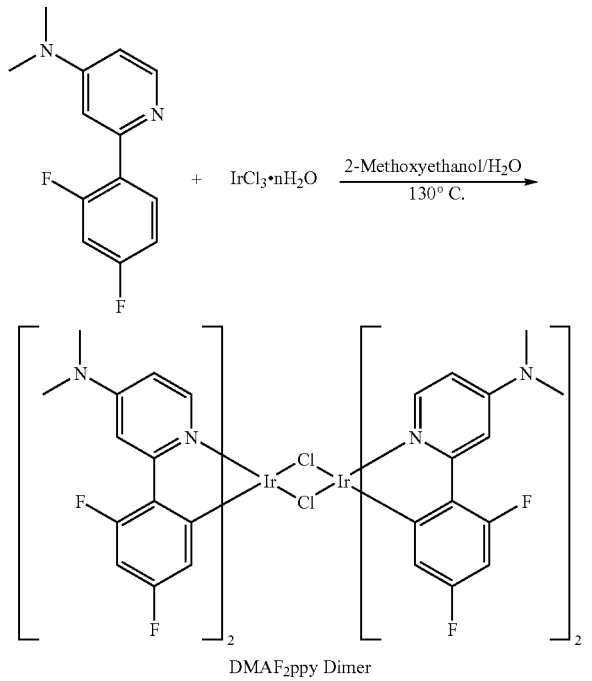

DMAF$_2$ppy Dimer

Except that 25.26 g(1.25×10$^4$ mmol) of a 2-bromo-4-dimethylaminopyridine was used instead of a 2-bromopyridine, a DMAF$_2$ppy dimer was synthesized by using the same method as in the reference example 1.

$^1$H-NMR(CD$_2$Cl$_2$, ppm): 8.7 (d, 4H), 7.5 (t, 4H), 6.3 (m, 4H), 6.1 (m, 4H) 5.4 (d, 4H), 3.2 (s, 24H).

Hereinafter, the methods of preparing a cyclometalated transition metal compound having a phosphorus ligand substituted with an alkyleneoxide according to the present invention, and a light emitting material having a phosphorus ligand substituted with an alkoxy according to the prior art will be described.

The NMR and TGA were performed for identifying the compounds of each example, and the PL and EL spectrum were analyzed for investigating the light emitting characteristics.

The light emitting characteristics was investigated by the following method.

After the compound was dissolved in a methylene chloride solution to give 10$^{-4}$ M solution, the light emitting characteristics at the state of the methylene chloride solution was investigated.

The EL display device used in measuring the light emitting characteristics has the following multilayer structure, and its light emitting area is 9 mm$^2$:

Substrate/first electrode/hole injecting layer/hole transporting layer/light emitting layer/hole blocking layer/electron transporting layer/electron injecting layer/second electrode (more specifically, glass/ITO/EDOT-PSS(50 nm)/BAlq (40 nm)/PS(24%)+mCP(70%)+Dopant(6%)(40 nm)/BAIQ (40 nm)/LiF(0.8 nm)/Al(200 nm).

Example 1

Preparation of Compound (1)

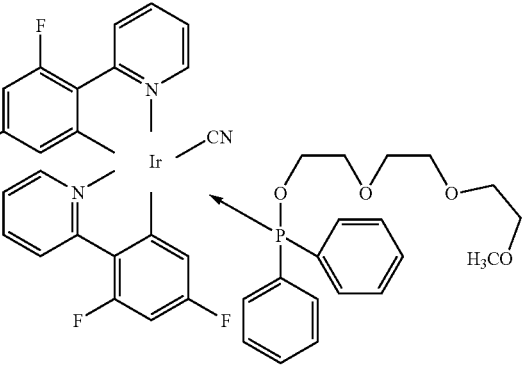

(1)

In the 100 ml 2-neck flask equipped with a thermometer, a mechanical stirrer and a reflux condenser, 0.5 g (0.411 mmol) of [(F$_2$ppy)$_2$IrCl]$_2$ prepared in the reference example 1 and 0.315 g (0.905 mmol) of P(Ph)$_2$(OC$_2$H$_4$)$_3$OCH$_3$ were dissolved in 50 ml of THF under nitrogen atmosphere, and stirred for about 24 hrs at room temperature. On completion of the reaction, the solvent was removed under reduced pressure, and then the reaction mixture was dissolved in a dichloromethane, and a column chromatography was performed using a silica gel, and a methanol and a dichloromethane as solvents. The resulting product was fully dried in a vacuum oven at 30□.

0.238 g (3.66 mmol) of a potassium cyanide were added to 0.5 g (0.523 mmol) of the product, the mixture was put into a mixed solvent containing 50 ml of THF and 30 ml of a methanol, and then the mixture was stirred for 24 hrs at room temperature. On completion of the reaction, the solvent was removed under reduced pressure, and then the reaction mixture was dissolved in a dichloromethane. Then, a column chromatography was performed using a silica gel, and a methanol and a dichloromethane as solvents, and then the resulting product was washed with a methanol and a dimethylether. Next, the product was recrystallized using a chloroform and a hexane, and then the solvent was removed by filtration. The resulting product was dried to give 0.38 g (yield: 76.7%) of white solid.

$^1$H NMR(CDCl$_3$, 400 MHz, δppm) 9.40 (1H, d), 9.20 (1H, d), 8.38 (1H, dd), 7.89 (3H, m), 7.58 (1H, d), 7.54 (2H, m), 7.47 (2H, m), 7.24 (2H, m), 7.05 (2H, t), 6.91 (1H, t), 6.81 (2H, t), 6.78 (2H, m), 5.82 (1H, dd), 5.40 (1H, t), 3.60 (1H, m), 3.50 (11H, m), 3.32 (3H, s).

Example 2

Preparation of Compound (2)

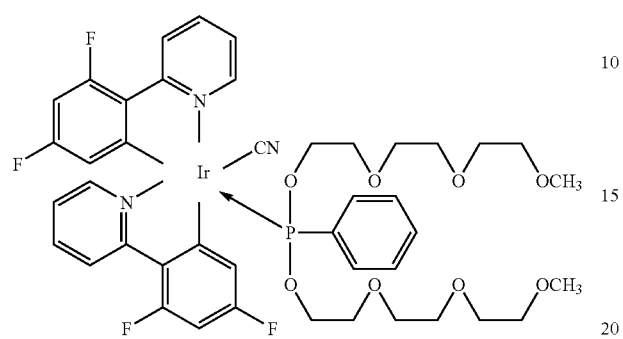

Except that a P(Ph)[(OC$_2$H$_4$)$_3$OCH$_3$]$_2$ was used instead of a P(Ph)$_2$(OC$_2$H$_4$)$_3$OCH$_3$, the compound (2) was synthesized in the same method as in the example 1. The yield of the compound (2) was 73.3%.

$^1$H NMR(CDCl$_3$, 400 MHz, δppm) 9.68 (1H, d), 9.27 (1H, d), 8.34 (1H, dd), 7.87 (2H, m), 7.62 (1H, t), 7.34 (1H, t), 7.20 (1H, t), 7.03 (3H, m), 6.78 (2H, t), 6.41 (2H, m), 5.77 (1H, dd), 5.41 (1H, t), 4.75 (1H, m), 4.27 (1H, m), 4.18 (1H, m), 3.79 (3H, m), 3.62 (14H, m), 3.49 (4H, m), 3.30 (3H, s).

Example 3

Preparation of Compound (3)

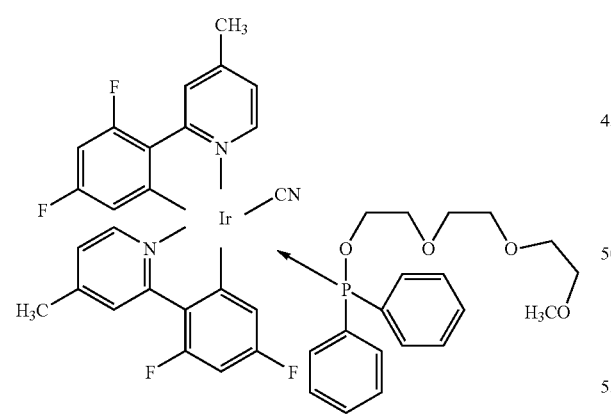

Except that a [(F$_2$pmp)$_2$IrCl]$_2$ was used instead of a dimer [(F$_2$ppy)$_2$IrCl]$_2$, the compound (3) was synthesized in the same method as in the example 1. The yield of the compound (3) was 81.5%.

$^1$H NMR(CDCl$_3$, 400 MHz, δppm) 9.18 (1H, d), 8.96 (1H, d), 8.21 (1H, s), 7.88 (2H, t), 7.59 (1H, s), 7.52 (1H, d), 7.47 (2H, m), 7.24 (1H, t), 7.05 (2H, t), 6.98 (1H, d), 6.81 (2H, t), 6.73 (1H, d), 6.43 (2H, m), 5.83 (1H, dd), 3.59 (1H, m), 3.49 (11H, m), 3.32 (6H, s), 2.58 (3H, s), 2.41 (3H, s).

Example 4

Preparation of Compound (4)

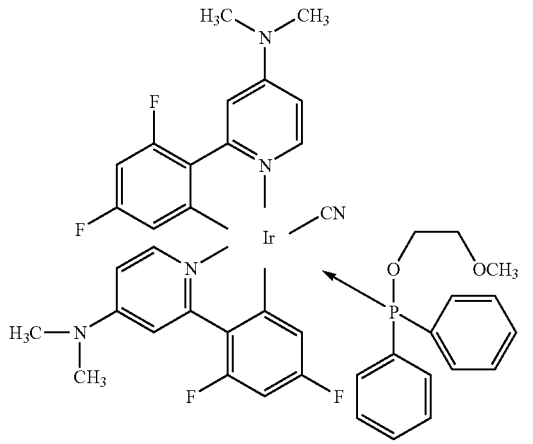

Except that a [(DMAF$_2$ppy)$_2$IrCl]$_2$ was used instead of a dimer [(F$_2$ppy)$_2$IrCl]$_2$, and a P(Ph)$_2$OC$_2$H$_4$OCH$_3$ instead of a ligand P(Ph)$_2$(OC$_2$H$_4$)$_3$OCH$_3$, the compound (4) was synthesized in the same method as in the example 1. The yield of the compound (4) was 62.5%.

$^1$H NMR(CDCl$_3$, 400 MHz, δppm) 8.76 (1H, d), 8.50 (1H, d), 7.88 (2H, t), 7.59 (1H, m), 7.45 (3H, m), 7.22 (1H, t), 7.07 (2H, m), 7.01 (1H, m), 6.90 (2H, t), 6.33 (3H, m), 6.08 (1H, dd), 5.91 (1H, dd), 3.87 (1H, t), 3.70 (1H, m), 3.52 (1H, m), 3.28 (2H, m), 3.30 (3H, s), 3.16 (6H, s), 3.04 (6H, s).

Example 5

Preparation of Compound (5)

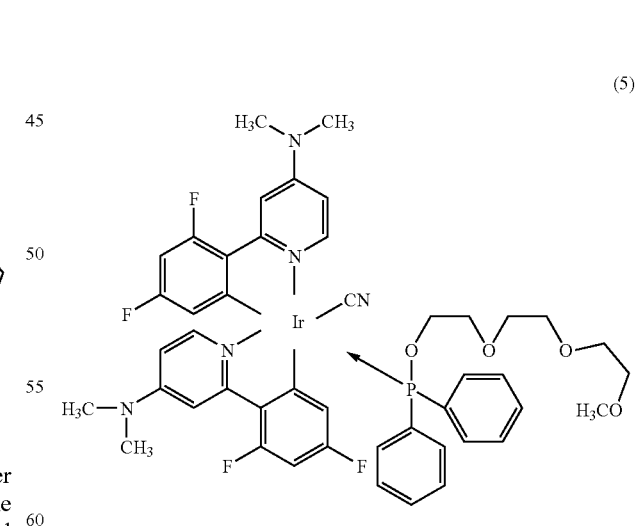

Except that a [(DMAF$_2$ppy)$_2$IrCl]$_2$ was used instead of a dimer [(F$_2$ppy)$_2$IrCl]$_2$, the compound (5) was synthesized in the same method as in the example 1. The yield of the compound (5) was 58.3%.

$^1$H NMR(CDCl$_3$, 400 MHz, δppm) 8.74 (1H, d), 8.50 (1H, d), 7.88 (2H, t), 7.59 (1H, m), 7.45 (3H, m), 7.22 (1H, t), 7.07

(2H, t), 7.01 (1H, m), 6.92 (2H, t), 6.33 (3H, m), 6.08 (1H, dd), 5.91 (1H, dd), 5.67 (1H, t), 3.70 (1H, m), 3.48 (11H, m), 3.46 (3H, s), 3.16 (6H, s), 3.04 (6H, s).

Example 6

Preparation of Compound (6)

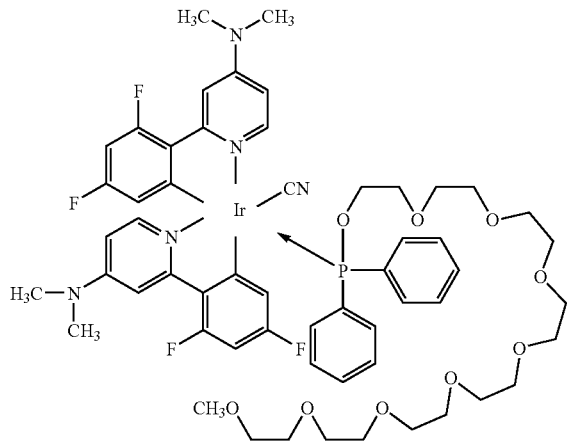

Except that a $[(DMAF_2ppy)_2IrCl]_2$ was used instead of a dimer $[(F_2ppy)_2IrCl]_2$, and a $P(Ph)_2(OC_2H_2)_8OCH_3$ instead of a ligand $P(Ph)_2(OC_2H_4)_3OCH_3$, the compound (6) was synthesized in the same method as in the example 1. The yield of the compound (6) was 48.1%.

$^1$H NMR(CDCl$_3$, 400 MHz, δppm) 8.73 (1H, d), 8.50 (1H, d), 7.86 (1H, t), 7.58 (1H, m), 7.41 (3H, m), 7.22 (1H, t), 7.07 (1H, t), 7.01 (1H, m), 6.92 (2H, t), 6.33 (3H, m), 6.08 (1H, dd), 5.91 (1H, dd), 5.67 (1H, t), 3.70 (1H, m), 3.50 (27H, m), 3.33 (3H, s), 3.16 (6H, s), 3.04 (6H, s).

The light emitting characteristics, the color coordinate and the degradation temperature of the phosphorescent light emitting material prepared in the examples were summarized in table 1 below.

TABLE 1

| Example | $\lambda_{max}$(nm) | Color coordinate (CIE) | Degradation temperature (□) |
|---|---|---|---|
| Example 1 | 446, 473 | 0.1486, 0.1625 | 247.4 |
| Example 2 | 444, 471 | 0.1486, 0.1567 | 292.7 |
| Example 3 | 444, 470 | 0.1493, 0.1517 | 250.7 |
| Example 4 | 432, 452 | 0.1506, 0.0945 | 286.1 |
| Example 5 | 432, 452 | 0.1506, 0.0970 | 257.8 |
| Example 6 | 432, 452 | 0.1511, 0.0984 | 298.2 |

As shown in table 1, the phosphorescent light emitting material incorporating a phosphorus ligand having an alkylene oxide substituent according to the present invention showed better heat stability than the phosphorescent light emitting material incorporating a phosphorus ligand having an alkoxy substituent according to the prior art, and its emitting wavelength was migrated to blue region.

Figure 2:
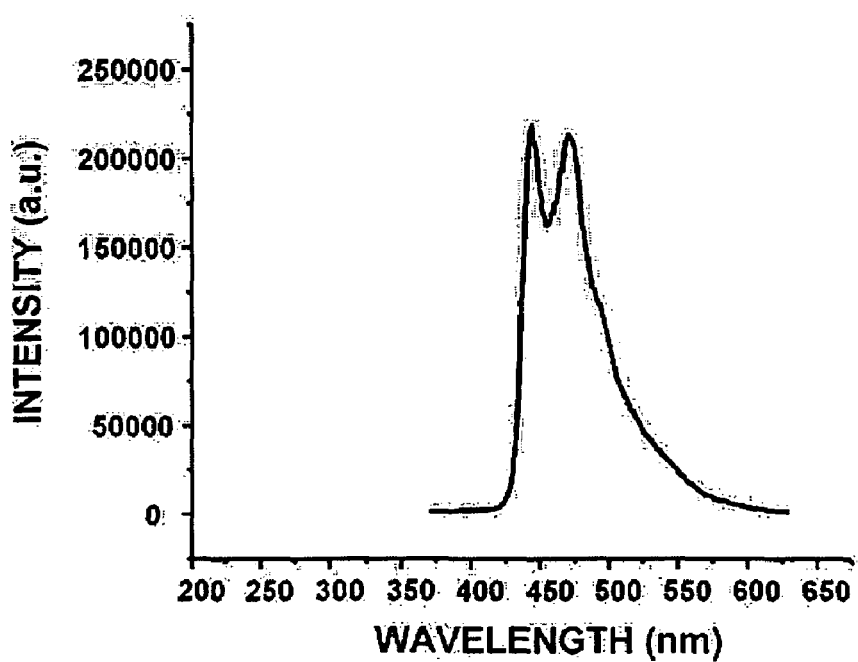
FIG. 2 is a PL spectrum of the compound according to the example 2 of the present invention.
Figure 3:
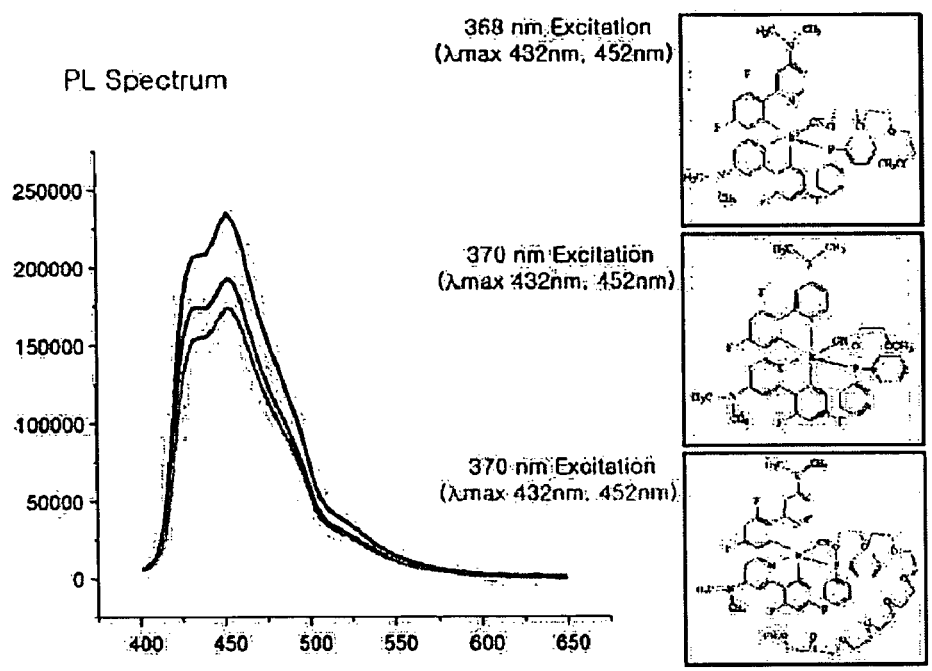
FIG. 3 is a PL spectrum of the compounds according to the examples 4, 5 and 6 of the present invention.
Figure 4:
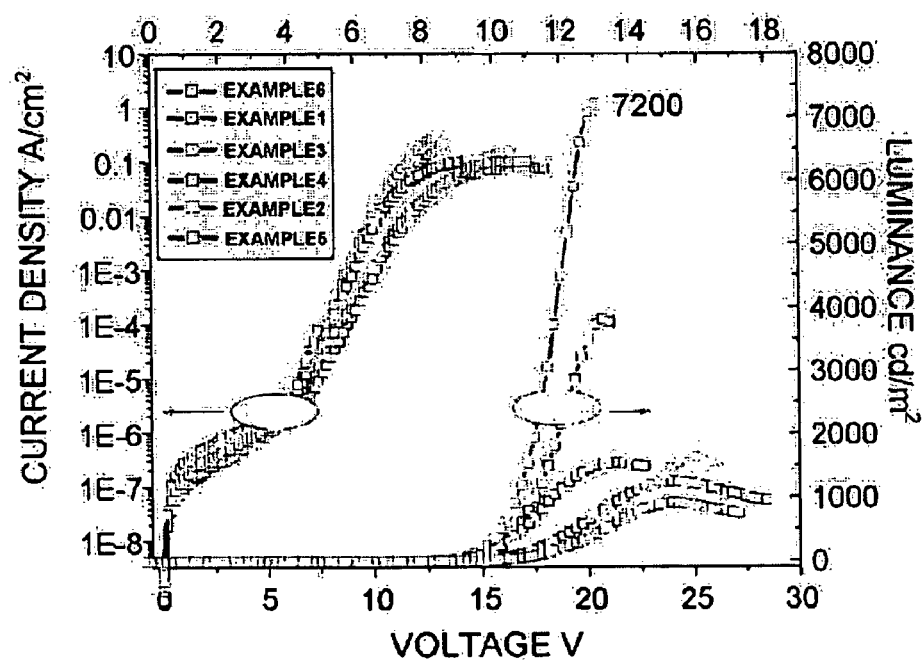
FIG. 4 is a graph showing the current density of the compounds according to the examples of the present invention.
Figure 5:
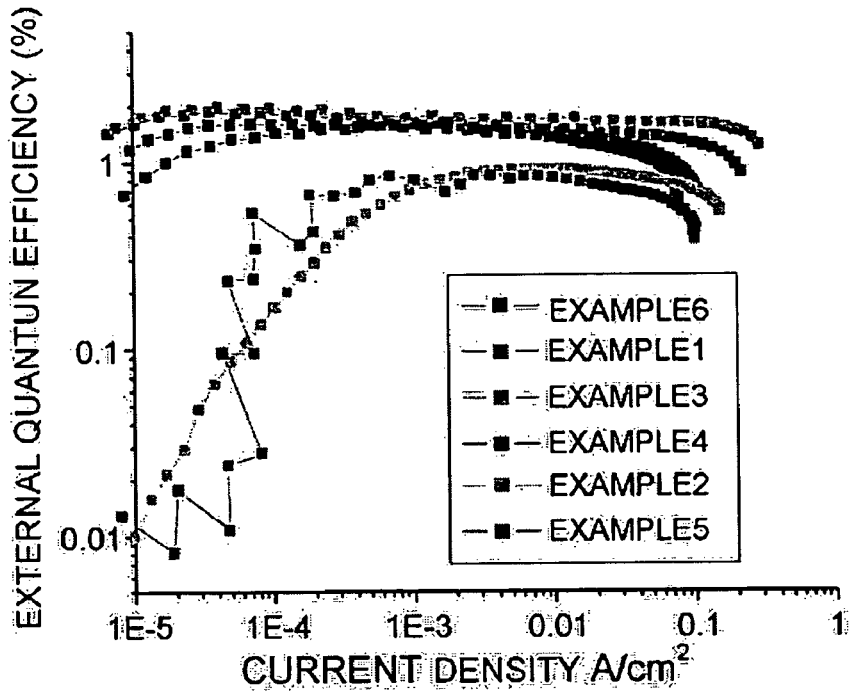
FIG. 5 is a graph showing the external quantum efficiency of the compounds according to the examples of the present invention.
Figure 6:
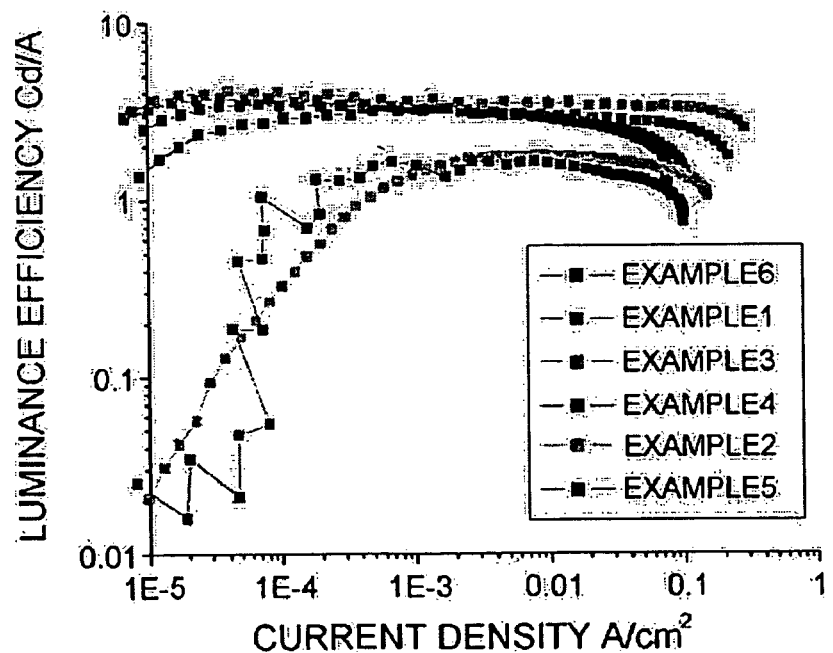
FIG. 6 is a graph showing the luminance efficiency of the compounds according to the examples of the present invention.
Figure 7:
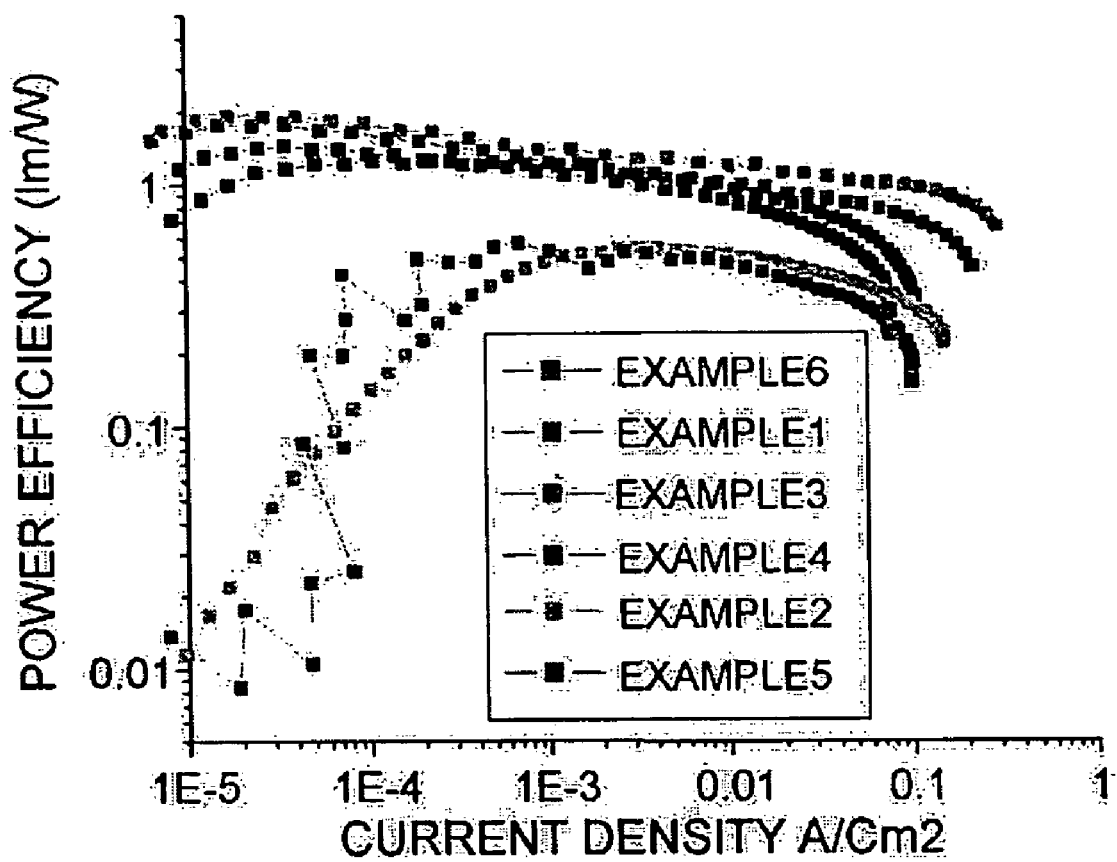
FIG. 7 is a graph showing the power efficiency of the compounds according to the examples of the present invention.

FIG. 1 is a photoluminescence (PL) spectrum of the compounds according to the examples 1, 3 and 5 of the present invention, FIG. 2 is a PL spectrum of the compound according to the example 2 of the present invention, FIG. 3 is a PL spectrum of the compounds according to the examples 4, 5 and 6 of the present invention, FIG. 4 is a graph showing the current density of the compounds according to the examples of the present invention, FIG. 5 is a graph showing the external quantum efficiency of the compounds according to the examples of the present invention, FIG. 6 is a graph showing the luminance efficiency of the compounds according to the examples of the present invention, and FIG. 7 is a graph showing the power efficiency of the compounds according to the examples of the present invention.

As shown in the table 1 and the Figures, it can be found that, when a phosphorus atom having an alkylene oxide substituent is incorporated as an ancillary ligand, a dopant having excellent phosphorescent characteristic is formed, and it is suitable as a blue phosphorescent material. Further, it can be found that, by incorporating various main ligands, a full color of red, green and blue can be embodied.

The cyclometalated transition metal complex according to the present invention can emit light at a wavelength range of from blue to red region efficiently from triplet MLCT, by incorporating a phosphorus ligand substituted with an alkylene oxide. This cyclometalated transition metal complex can be employed when forming an organic film of an organic electroluminescent display device, can emit light at a wavelength range of 400 nm to 650 nm as a phosphorescent material having high efficiency, and can emit white light as well when used with a green light emitting material and a red light emitting material.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A cyclometalated transition metal complex represented by Formula I:

$$[C^\wedge N]_{n1}M[P(Y^1)_{n2}(R^2)_{3-n2}]_{3-n1}X \qquad (I)$$

wherein M is a transition metal;
C^N is a cyclometalated ligand;
n1 is 1 or 2;
n2 is an integer of 1 to 3;
$Y^1$ is an alkylene oxide represented by Formula II:

$$-(OR^2)_{n3}OR^3 \qquad (II)$$

wherein $R^2$ is a $C_2$-$C_{10}$ alkylene, $R^3$ is a hydrogen atom, a $C_1$-$C_{30}$ alkyl group, a $C_5$-$C_{14}$ cycloalkyl group, a $C_1$-$C_{20}$ aryl group, a $C_3$-$C_1$, heterocyclic or methacrylate group, and n3 is an integer of 1 to 21;
$R^1$ is selected from the group consisting of a hydrogen atom, an alkyl group, an alkynyl group, an aryl group, an amino group, an alkoxy group, an aryloxy group, an acyl group, an alkoxycarbonyl group, an acyloxy group, an acylamino group, an alkoxycarbonylamino group, an aryloxycarbonylamino group, a sulfonylamino group, a sulfamoyl group, a carbamoyl group, an arylthio group, a heteroarylthio group, a sulfonyl group, a sulfinyl group, an ureido group, a phosphoramido group, a hydroxy group, a mercapto group, a halogen atom, a cyano group, a sulfo group, a carboxy group, a nitro group, a hydroxaminic group, a heterocyclic group, a silyl group, and a phosphino group; and
X is selected from the group consisting of Cl, OCN, CN, SCN, P(Ph)$_2$, R'COOH, R'CONH, R'NH, a pyrazole, a substituted or unsubstituted alkyl, alkoxy or aryloxy group, NR'H, NR'$_2$, OH, SH and a sulfonic acid group, wherein R' is a $C_1$-$C_{10}$ alkyl group, a $C_1$-$C_{14}$ cycloalkyl group or a $C_5$-$C_{14}$ aryl group.

2. The cyclometalated transition metal complex of claim 1, wherein each C^N of the [C^N]$_{n1}$ is independently selected from the group consisting of the formulae IIIa through IIIz:
IIIa
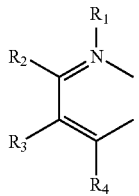
IIIb
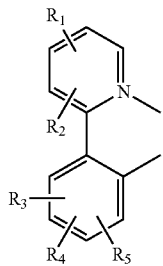
IIIc
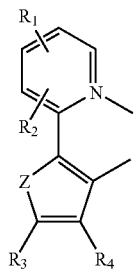
IIId
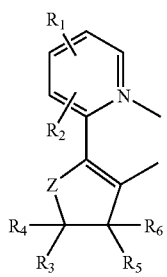
IIIe
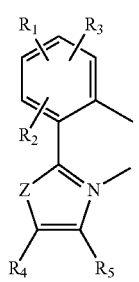
IIIf
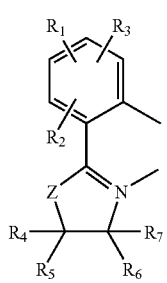
-continued
IIIg
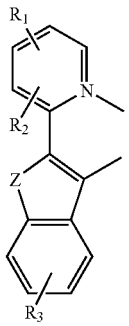
IIIh
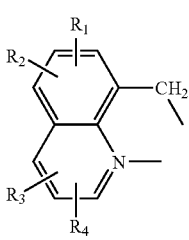
IIIi
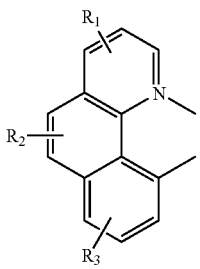
IIIj
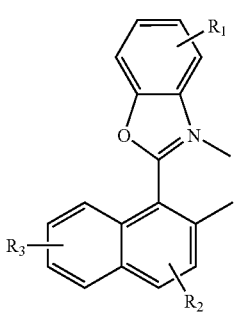
IIIk
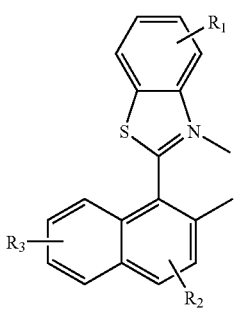

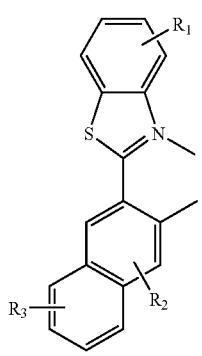 IIIl
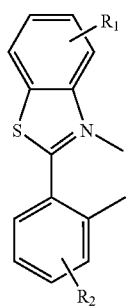 IIIm
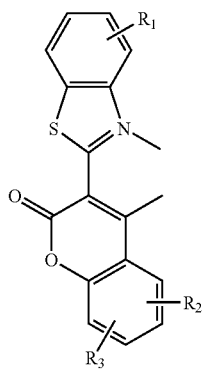 IIIn
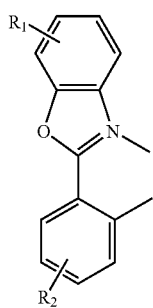 IIIo
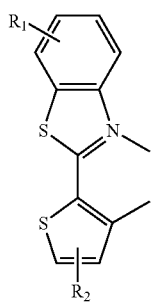 IIIp
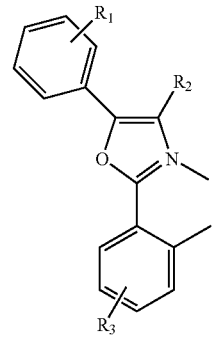 IIIq
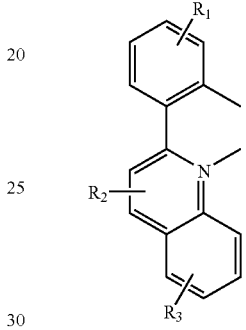 IIIr
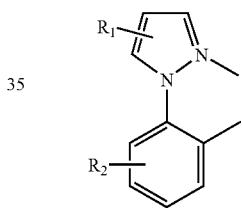 IIIs
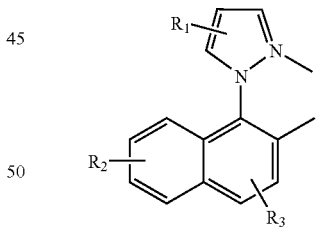 IIIt
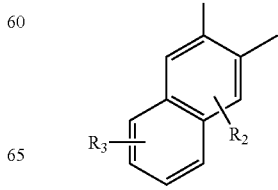 IIIu

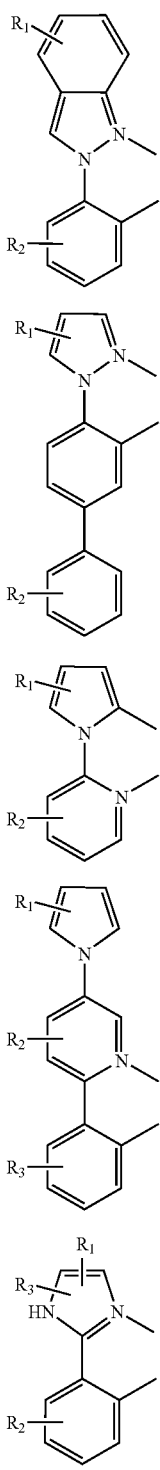

wherein Z is S, O or NR$_1$; and

R$_1$, R$_2$, R$_3$, R$_4$, R$_5$ and R$_6$ are each independently selected from the group consisting of a hydrogen atom, a halogen atom, CN, a silyl group, an alkyl group, an aryl group, an arylene group, an amino group, an alkoxy group, an aryloxy group, a heterocyclicoxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclicthio group, a sulfonyl group, a sulfinyl group, an ureido group, a phosphor amide group, a sulfino group, a hydrazino group, an imino group, a heterocyclic group, a silyloxy group, a hydroxamine group, a nitro group, a hydroxyl group, a mercapto group, a sulfo group, a carboxyl group and a nitro group, and at least two of R$_1$, R$_2$, R$_3$, R$_4$, R$_5$ and R$_6$ may be bound each other.

3. The cyclometalated transition metal complex of claim 1, wherein the M is Ru, Rh, Ir, Os, Pt or Au.

4. The cyclometalated transition metal complex of claim 1, wherein the M is Ir(III).

5. The cyclometalated transition metal complex of claim 1, wherein the complex emits light at a wavelength range of 400 nm to 650 nm.

6. The cyclometalated transition metal complex of claim 1, wherein the complex is any one selected from the group consisting of compounds below:

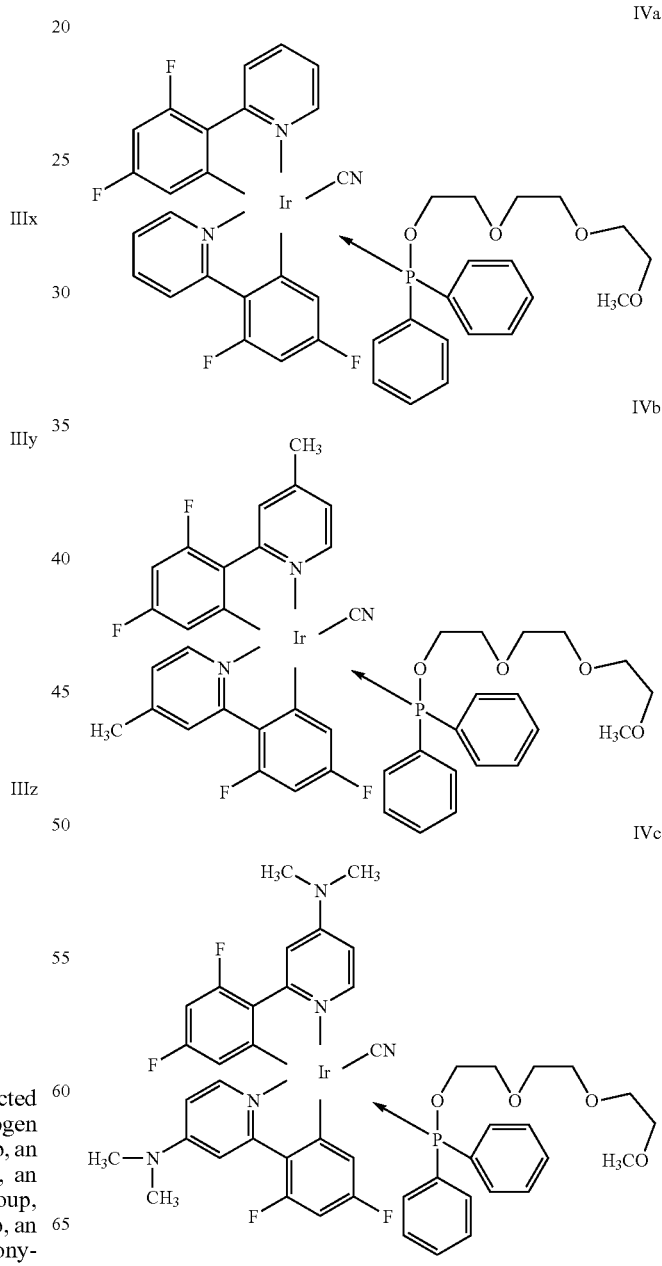

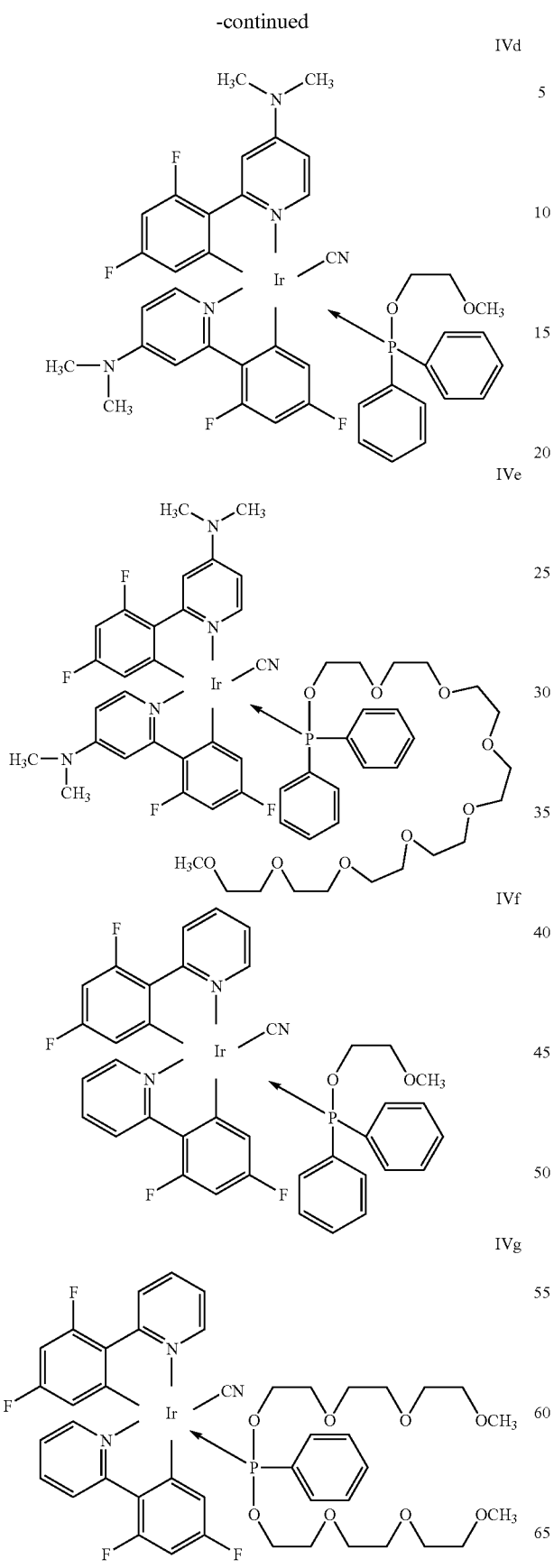

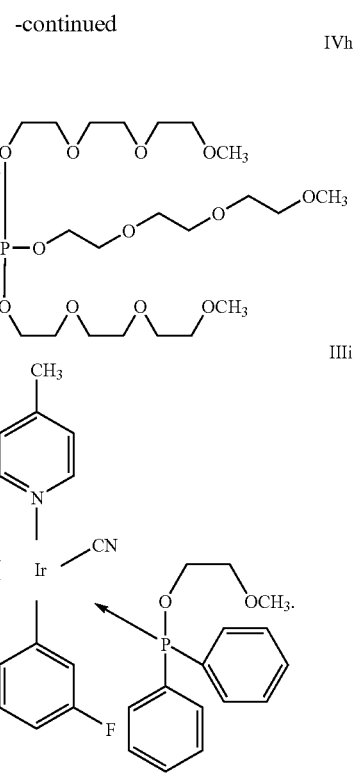

7. An organic electroluminescent device comprising an organic film between a pair of electrodes, wherein the organic film comprises the cyclometalated transition metal complex of claim 1.

8. A light-emitting device, comprising:
a pair of electrodes; and
an organic film between the pair of electrodes, the organic film comprising a cyclometalated transition metal complex represented by Formula I:

$$[C^\wedge N]_{n1}M[P(Y^1)_{n2}(R^1)_{3-n2}]_{3-n1}X \quad (I)$$

wherein M is a transition metal;
C^N is a cyclometalated ligand;
n1 is 1 or 2;
n2 is an integer of 1 to 3;
$Y^1$ is an alkylene oxide represented by Formula II:

$$-(OR^2)_{n3}OR^3 \quad (II)$$

wherein $R^2$ is a $C_2$-$C_{10}$ alkylene, $R^3$ is a hydrogen atom, a $C_1$-$C_{30}$ alkyl group, a $C_5$-$C_{14}$ cycloalkyl group, a $C_5$-$C_{20}$ aryl group, a $C_3$-$C_{15}$ heterocyclic or methacrylate group, and n3 is an integer of 1 to 21;
$R^1$ is selected from the group consisting of a hydrogen atom, an alkyl group, an alkynyl group, an aryl group, an amino group, an alkoxy group, an aryloxy group, an acyl group, an alkoxycarbonyl group, an acyloxy group, an acylamino group, an alkoxycarbonylamino group, an aryloxycarbonylamino group, a sulfonylamino group, a sulfamoyl group, a carbamoyl group, an arylthio group, a heteroarylthio group, a sulfonyl group, a sulfinyl group, an ureido group, a phosphoramido group, a hydroxy group, a mercapto group, a halogen atom, a cyano group, a sulfo group, a carboxy group, a nitro group, a hydroxaminic group, a heterocyclic group, a silyl group, and a phosphino group; and
X is selected from the group consisting of Cl, OCN, CN, SCN, P(Ph)$_2$, R'COOH, R'CONH, R'NH, a pyrazole, a substituted or unsubstituted alkyl, alkoxy or aryloxy group, NR'H, NR'$_2$, OH, SH and a sulfonic acid group, wherein R' is a $C_1$-$C_{10}$ alkyl group, a $C_5$-$C_{14}$ cycloalkyl group or a $C_5$-$C_{14}$ aryl group.

9. The light-emitting device of claim 8, wherein each C^N of the [C^N]$_{n1}$ is independently selected from the group consisting of the formulae IIIa through IIIz:

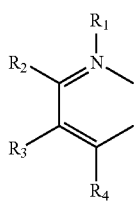
IIIa

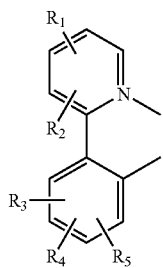
IIIb

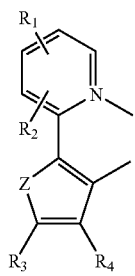
IIIc

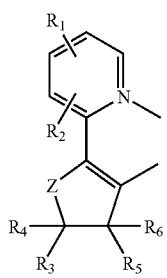
IIId

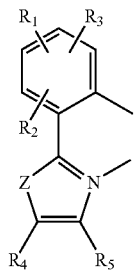
IIIe

-continued

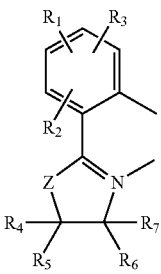
IIIf

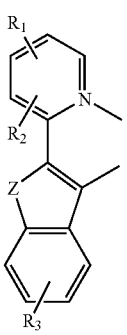
IIIg

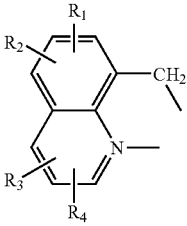
IIIh

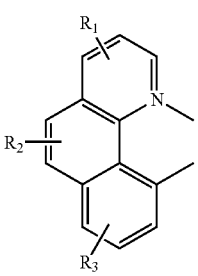
IIIi

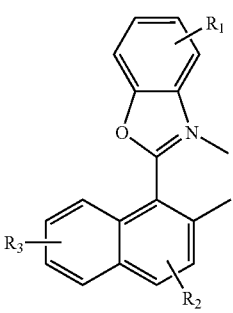
IIIj

-continued
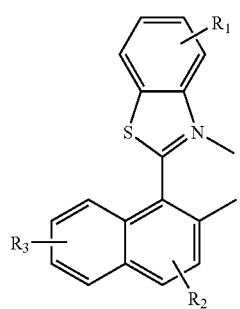
IIIk
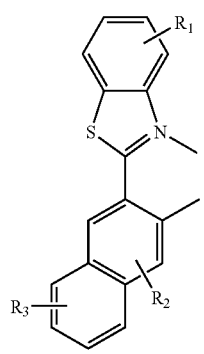
IIIl
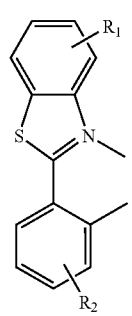
IIIm
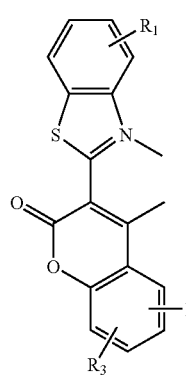
IIIn
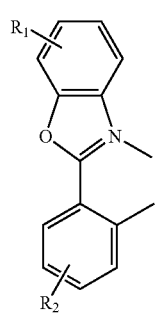
IIIo
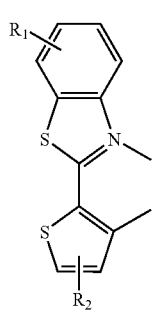
IIIp
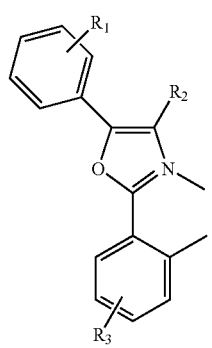
IIIq
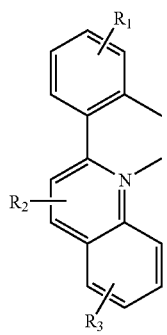
IIIr
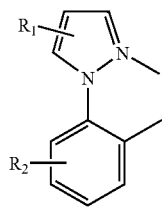
IIIs
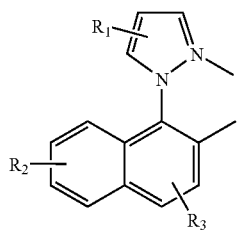
IIIt -continued

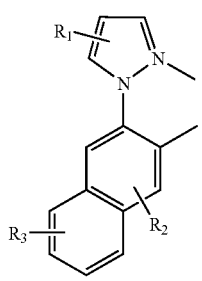
IIIu

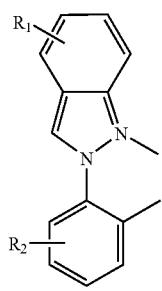
IIIv

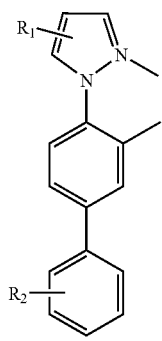
IIIw

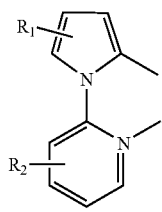
IIIx

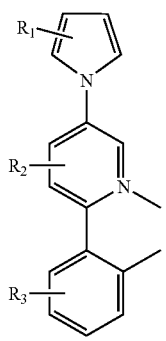
IIIy

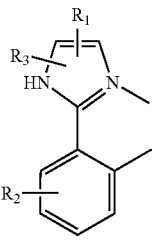
IIIz wherein Z is S, O or $NR_1$; and $R_1$, $R_2$, $R_3$, $R_4$, $R_5$ and $R_6$ are each independently selected from the group consisting of a hydrogen atom, a halogen atom, CN, a silyl group, an alkyl group, an aryl group, an arylene group, an amino group, an alkoxy group, an aryloxy group, a heterocyclicoxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclicthio group, a sulfonyl group, a sulfinyl group, an ureido group, a phosphor amide group, a sulfino group, a hydrazino group, an imino group, a heterocyclic group, a silyloxy group, a hydroxamine group, a nitro group, a hydroxyl group, a mercapto group, a sulfo group, a carboxyl group and a nitro group, and at least two of $R_1$, $R_2$, $R_3$, $R_4$, $R_5$ and $R_6$ may be bound each other.

10. The light-emitting device of claim 8, wherein the M is Ru, Rh, Ir, Os, Pt or Au.

11. The light-emitting device of claim 8, wherein the M is Ir(III).

12. The light-emitting device of claim 8, wherein the complex emits light at a wavelength range of 400 nm to 650 nm.

13. The light-emitting device of claim 8, wherein the complex is any one selected from the group consisting of compounds represented by Formulae IVa through IVi:

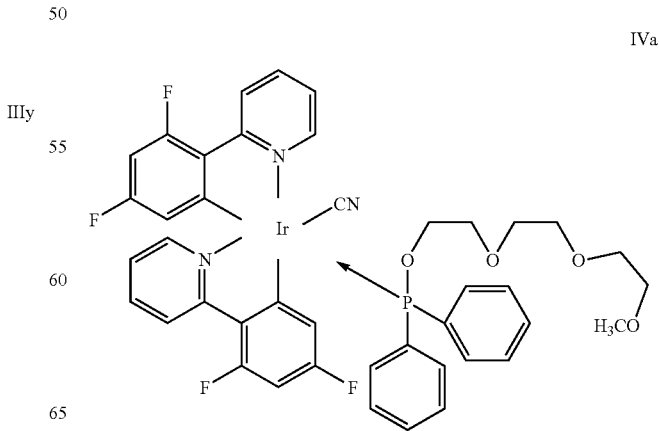
IVa

IVb
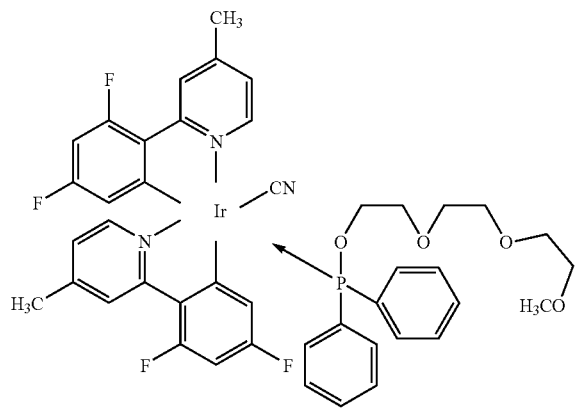
IVc
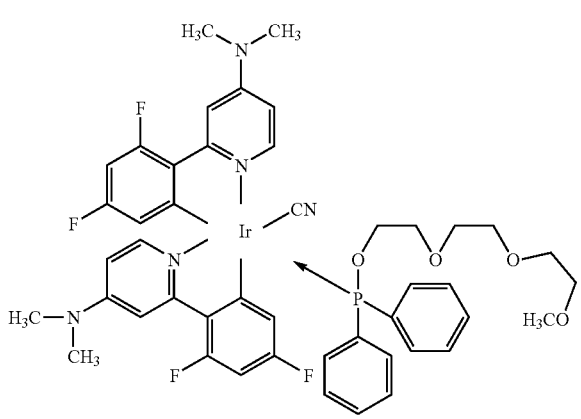
IVd
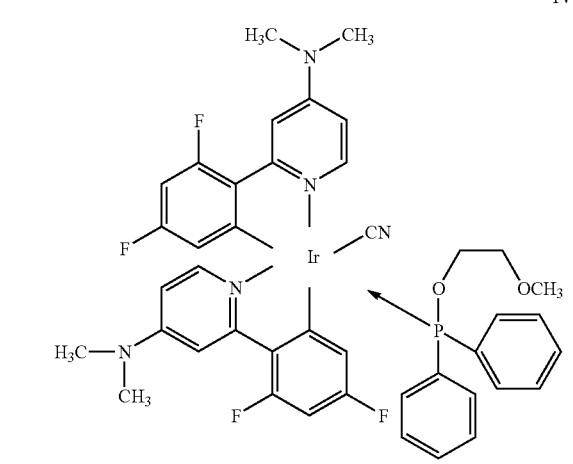
IVe
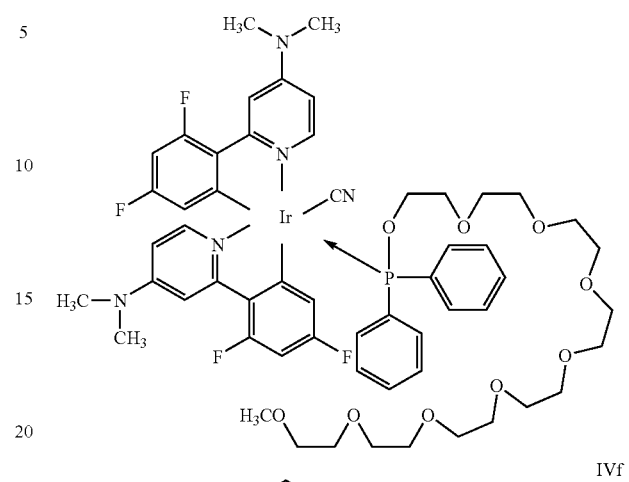
IVf
IVg
IVh

14. The light-emitting device of claim 8, wherein the organic film further comprises at least one selected from the group consisting of at least one of polymer hosts, a mixed host of a polymer and a low molecular weight host, a low molecular weight host, and a non-luminescent polymer matrix.

15. The light-emitting device of claim 8, wherein the organic film further comprises a green light emitting material and a red light emitting material.

16. An organic electroluminescent device, comprising:
a pair of electrodes; and
an organic layer interposed between the electrodes, the organic layer comprising a cyclometalated transition metal, the cyclometalated transition metal complex is represented by Formula I:

$$[C\char`\^N]_{n1}M[P(Y^1)_{n2}(R^1)_{3-n2}]_{3-n1}X \qquad (I)$$

wherein M is M is Ru, Rh, Ir, Os, Pt or Au;
C^N is a cyclometalated ligand, each C^N of the $[C\char`\^N]_{n1}$ being independently selected from the group consisting of the formulae IIIa through IIIz:

-continued
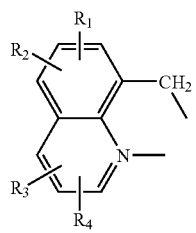
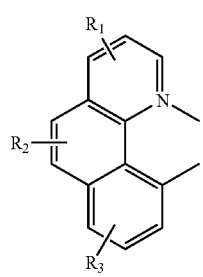
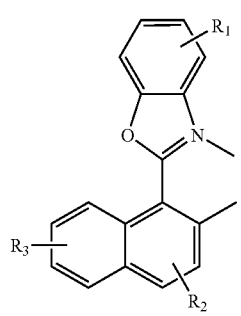 IIIj
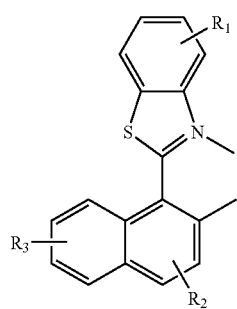 IIIk
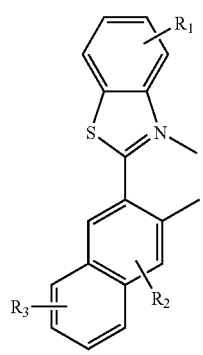 IIIl
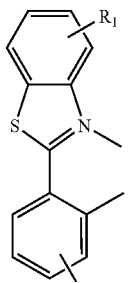 IIIh
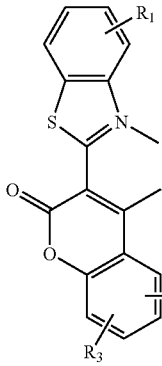 IIIi
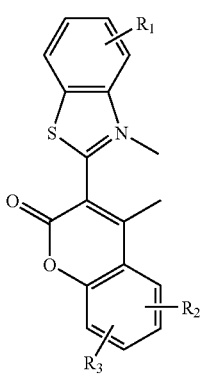
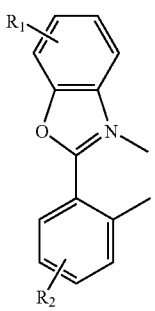 IIIm
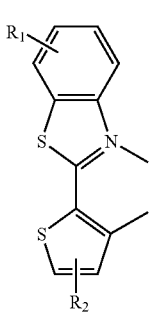 IIIn
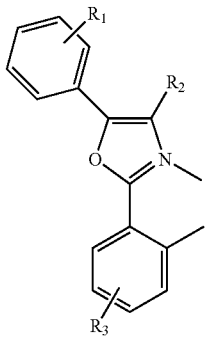 IIIo
IIIp
IIIq

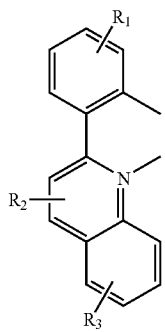

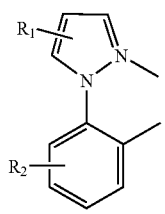

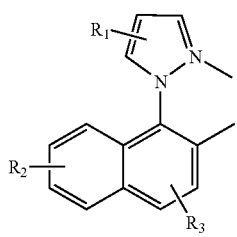

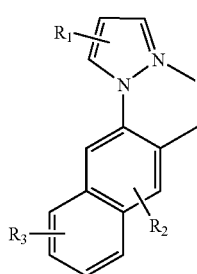

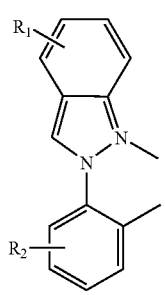

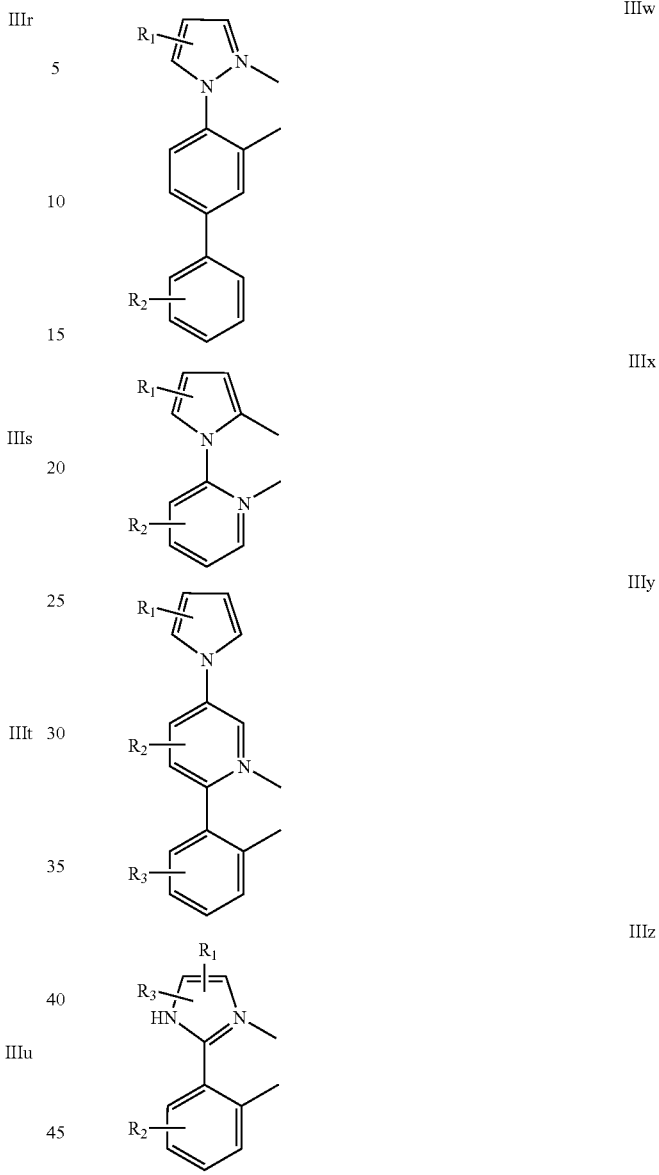

wherein Z is S, O or NR$_1$; and

R$_1$, R$_2$, R$_3$, R$_4$, R$_5$ and R$_6$ are each independently selected from the group consisting of a hydrogen atom, a halogen atom, CN, a silyl group, an alkyl group, an aryl group, an arylene group, an amino group, an alkoxy group, an aryloxy group, a heterocyclicoxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclicthio group, a sulfonyl group, a sulfinyl group, an ureido group, a phosphor amide group, a sulfino group, a hydrazino group, an imino group, a heterocyclic group, a silyloxy group, a hydroxamine group, a nitro group, a hydroxyl group, a mercapto group, a sulfo group, a carboxyl group and a nitro group, and at least two of R$_1$, R$_2$, R$_3$, R$_4$, R$_5$, and R$_6$ may be bound each other;

n1 is 1 or 2;

n2 is an integer of 1 to 3;

$Y^1$ is an alkylene oxide represented by Formula II:

$$—(OR^2)_{n3}OR^3 \quad (II)$$

wherein $R_2$ is a $C_2$-$C_{10}$ alkylene, $R_3$ is a hydrogen atom, a $C_1$-$C_{30}$ alkyl group, a $C_5$-$C_{14}$ cycloalkyl group, a $C_5$-$C_{20}$ aryl group, a $C_3$-$C_{15}$ heterocyclic or methacrylate group, and n3 is an integer of 1 to 21;

$R^1$ is selected from the group consisting of a hydrogen atom, an alkyl group, an alkynyl group, an aryl group, an amino group, an alkoxy group, an aryloxy group, an acyl group, an alkoxycarbonyl group, an acyloxy group, an acylamino group, an alkoxycarbonylamino group, an aryloxycarbonylamino group, a sulfonylamino group, a sulfamoyl group, a carbamoyl group, an arylthio group, a heteroarylthio group, a sulfonyl group, a sulfinyl group, an ureido group, a phosphoramido group, a hydroxy group, a mercapto group, a halogen atom, a cyano group, a sulfo group, a carboxy group, a nitro group, a hydroxaminic group, a heterocyclic group, a silyl group, or a phosphino group; and X is selected from the group consisting of Cl, OCN, CN, SCN, P(Ph)$_2$, R'COOH, R'CONH, R'NH, a pyrazole, a substituted or unsubstituted alkyl, alkoxy or aryloxy group, NR'H, NR'$_2$, OH, SH and a sulfonic acid group, wherein R' is a $C_1$-$C_{10}$ alkyl group, a $C_5$-$C_{14}$ cycloalkyl group or a $C_5$-$C_{14}$ aryl group.

17. The organic electroluminescent device of claim 16, wherein the transition metal atom is Ir(III).

18. The organic electroluminescent device of claim 16, wherein the organic layer is a light emitting layer.

19. The organic electroluminescent device of claim 16, wherein the organic film further comprises a green light emitting material and a red light emitting material to emit white light.

\* \* \* \* \*